United States Patent
Zahrly et al.

(10) Patent No.: US 9,125,699 B2
(45) Date of Patent: Sep. 8, 2015

(54) POLYAXIAL FASTENER SYSTEMS AND METHODS

(75) Inventors: Daniel C. Zahrly, Germantown, TN (US); David Edward Chreene, Hernando, MS (US); Charles R. Baker, Lakeland, TN (US); Sied W. Janna, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 783 days.

(21) Appl. No.: 13/320,572

(22) PCT Filed: May 14, 2010

(86) PCT No.: PCT/US2010/034996
§ 371 (c)(1),
(2), (4) Date: Jan. 17, 2012

(87) PCT Pub. No.: WO2010/132830
PCT Pub. Date: Nov. 18, 2010

(65) Prior Publication Data
US 2012/0136396 A1 May 31, 2012

Related U.S. Application Data

(60) Provisional application No. 61/178,633, filed on May 15, 2009.

(51) Int. Cl.
*A61B 17/80* (2006.01)
*A61B 17/86* (2006.01)

(52) U.S. Cl.
CPC ......... *A61B 17/8057* (2013.01); *A61B 17/8047* (2013.01); *A61B 17/8605* (2013.01)

(58) Field of Classification Search
CPC ........... A61B 17/8057; A61B 17/8605; A61B 17/8047; A61B 17/8038
USPC ........... 606/78, 289, 290, 291, 305, 306, 319
See application file for complete search history.

(56) References Cited

U.S. PATENT DOCUMENTS

2005/0033298 A1* 2/2005 Hawkes et al. ............. 606/61
2006/0009771 A1 1/2006 Orbay et al.
(Continued)

FOREIGN PATENT DOCUMENTS

| WO | WO0066012 A1 | 11/2000 |
|----|----|----|
| WO | WO2006089145 A1 | 8/2006 |
| WO | WO2007014279 A3 | 7/2007 |
| WO | WO2007075454 A1 | 7/2007 |
| WO | WO2008051707 A2 | 5/2008 |

OTHER PUBLICATIONS

Authorized Officer Jang, Ki Wan, International Search Report/Written Opinion in PCT/US2010/034996, mailed Jan. 24, 2011, 8 pages.

(Continued)

*Primary Examiner* — Christopher Beccia
*Assistant Examiner* — Diana S Jones
(74) *Attorney, Agent, or Firm* — Fish & Richardson P.C.

(57) ABSTRACT

Systems for reducing a fracture in a bone, comprising a bone plate and a polyaxial fastener. In some examples the head of the polyaxial fastener has a deformable portion. As a fastener is inserted into an opening of a bone plate, threads located within the opening deform the deformable portion to secure the fastener in place at a desired angle within the opening. The head of the fastener also includes a bottom portion that bears against a portion of the opening to move the bone plate relative to the underlying tissue. A securing member or other structure may be included at the interface of the head and the deformable portion to secure the deformable portion to the head. At least one flute may be included on the deformable portion that provides a lead-in for the threads within the opening to cut into the deformable portion.

49 Claims, 23 Drawing Sheets

(56) References Cited

U.S. PATENT DOCUMENTS

2006/0122602 A1 6/2006 Konieczynski et al.
2006/0200147 A1* 9/2006 Ensign et al. .................. 606/69
2008/0177330 A1* 7/2008 Ralph et al. .................. 606/290
2008/0319490 A1 12/2008 Jackson

OTHER PUBLICATIONS

Notice of Reasons for Rejection for Japanese Application No. 2012-511056, mailed Jan. 7, 2014.
First Office Action for Chinese Application No. 201080031537.4, mailed Nov. 22, 2013.
Office Action in Russian Application No. 2011149998/14, mailed Feb. 26, 2014.
Extended European Search Report for European Application No. 10775633.0, mailed Nov. 26, 2013.
Patent Examination Report No. 1 for Australian Application No. 2010248816, mailed Nov. 28, 2014.
Second Office Action for Chinese Application No. 201080031537.4, mailed Oct. 16, 2014.

* cited by examiner

POLYAXIAL FASTENER SYSTEMS AND METHODS

CROSS REFERENCE TO RELATED APPLICATIONS

This application claims priority to and the full benefit of U.S. Provisional Application Ser. No. 61/178,633, filed May 15, 2009 and titled "Polyaxial Fastener Systems and Methods," the entire contents of which are incorporated herein by reference.

TECHNICAL FIELD

This disclosure relates to orthopedic fixation devices and bone plating systems for fracture fixation.

BACKGROUND

Bone fractures are often repaired by securing a bone plate across the fracture. Depending upon which bone is to be treated, the bone plate may be straight or curved to match the contour of the bone for which it is designed. Bone plates may also be provided in many shapes and sizes. In cases where a bone is severely comminuted or if bone segments are missing, the use of bone plate and screw systems promotes healing of the fracture by providing a rigid fixation or support structure for the bone.

Bone plates may be secured to the bone in a number of ways. An existing solution is a plate and screw system where screws having threaded heads, called locking screws, are locked in the plate. The locking screw is threaded through an opening in the plate and into the bone. The locking screw is then secured to the bone plate via threads in the screw head that cooperate with threaded openings in the bone plate. Because the threads on the head of the locking screw interdigitate with threads in the plate, the plate and screws(s) form one stable system and secure the plate with respect to the bone in rigid fixation. Locking screws can achieve angular and axial stability and eliminate the possibility for the screws to toggle, slide, or become dislodged in situ, thereby reducing the risk of postoperative loss of fracture reduction.

Although locking screws may reduce the incidence of loosening, the threads on the head of a locking screw properly engage the threads of an opening only when the locking screw is inserted in a single angular orientation pre-determined by the axis of the threaded opening. Given this uniaxial relationship, locking screws have limited versatility.

One such example of limited use occurs when treating a comminuted fracture where multiple bone fragments are in irregular positions or otherwise displaced. Although a surgeon may wish to obtain the benefits of a locking screw, the pre-determined angle at which the locking screw extends from the plate may not be the angle that would allow the surgeon to "grab" (or seize, or otherwise secure) a desired bone fragment. In this case, the surgeon may need to secure the plate to the bone somewhere else or use a non-locking screw.

A non-locking screw has a head that is not threaded, but is instead round and smooth. Non-locking screws can be used in either threaded openings or non-threaded openings. Because there are no threads on the head, a non-locking screw is not threaded with or secured to the plate. Thus, one advantage of non-locking screws is that they can be inserted at various angles because they are not limited by the threaded engagement of locking screws with the bone plate. Non-locking screws present some disadvantages, however. For example, a non-locking screw is not optimal if the surgeon desires the rigid stable construct of a locking screw and plate. Non-locking screws can loosen, causing the screw to toggle, slide, or become dislodged.

There are bone plating systems that provide the surgeon with the option of choosing a non-locking or a locking screw. Some systems provide plates with both threaded holes (that may receive either locking screws or non-locking screws) and non-threaded holes (for non-locking screws). There are also systems that provide partially threaded slots to allow either non-locking or locking screws to be used interchangeably in the same slot. Such combination slots provide surgeons with the intra-operative choice about whether to use the plate with locking screws, non-locking screws, or with a combination of both. These combination slots typically have a partially threaded opening that can receive either a compression screw or a locking screw. Because these combination slots are only partially threaded, however, the locking screw(s) may not be able to maintain the fixed angular relationship between the screw(s) and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intra-operative plate orientation. Moreover, the locking screw can still only be inserted at a single angle—the predetermined angle defined by the manufacturer.

Additionally, current bone plate and screw systems still limit a surgeon's ability to both lock a fastener with respect to the bone plate, but still allow the fastener to extend from the bone plate at various angles. Locking screws lock into the plate, but only in a single angular configuration, and non-locking screws allow various angle configurations, but they do not provide a stable construct with the plate. Accordingly, none of these options allow a surgeon to capture bone fragments that do not align with the axis of the opening provided on the plate in a rigid fashion. Thus, currently available options can still lead to misalignment and poor clinical results.

There have been some attempts to provide polyaxial locking systems. One effort includes providing holes that accept fixed angle locking pegs and multidirectional locking pegs, with a threaded cap inserted over the multidirectional peg to hold it in the desired angular orientation within the hole. Such a system can be cumbersome to use because, although the multidirectional peg can be inserted at any angle, the surgeon then needs to thread a small cap onto the top of the peg head and into the plate, requiring an extra step, extra time, and extra instrumentation. Such systems also fail to allow the use of non-locking members in conjunction with the locking and multidirectional pegs.

Other systems that have attempted to offer polyaxial fixation include providing a bone plate with inserts at the hole peripheries made out of a deformable material, with the remaining part of the plate made of titanium. The plate is manufactured and the inserts are then pushed into the hole peripheries. When screws are inserted, the inserts are compressed between the screw heads and the edges of the plate's holes, thereby holding the screws and inserts in place. Challenges with such systems are that they cannot be used with non-locking screws and plates with deformable inserts are more expensive to manufacture than regular bone plates. Accordingly, there exists a need for an improved bone plating system that overcomes the deficiencies of the prior art. In particular, there exists a need to provide a plating system that allows the surgeon to choose the angle at which a screw or fastener is inserted through, and rigidly affixed in, an opening of a bone plate.

SUMMARY

Implementations described herein provide polyaxial fasteners that may be inserted at any one of a plurality of insertion angles within an opening of a bone plate. In one implementation the head of the polyaxial fastener has a deformable portion. As the fastener is inserted into the opening of the bone plate and torque is applied to the fastener, the deformable portion comes into contact with a set of threads within the opening. The threads are made from a material that is harder than the deformable portion of the fastener. Thus, the threads cut into and deform the deformable portion, forming a secure fit between the polyaxial fastener and the plate.

The polyaxial fastener may be inserted into the opening of the bone plate at any one of a plurality of insertion angles because there is not a pre-formed set of threads on the head of the fastener. Rather, threads are formed on the polyaxial fastener at any desired insertion angle upon engagement with the threads of the opening of the bone plate. The polyaxial fasteners thus allow surgeons to capture bone fragments that are in various positions, for example, in cases of severe fractures with highly fragmented bones. Additionally, the polyaxial fasteners provide a stable connection between the bone, bone plate, and reduce the likelihood that the fastener will become loose and detach from the bone and/or bone plate.

In one general aspect, a fastener for engagement with bone includes a bone engaging portion, a head portion, a deformable portion that contacts the head portion, and a retaining structure that retains the deformable portion in contact with the head portion by a force that includes a non-frictional component. The, deformable portion includes a material that deforms when the fastener engages one or more fastener-engaging structures of a stabilizing structure.

Implementations may include one or more of the following features. For example, the deformable portion includes at least one of polyetheretherketone, polyether ketone ketone, self-reinforced polyphenylene, polyphenylsulfone, polysulfone, polyethylene, ultra-high molecular weight polyethylene, a carbon composite, resorbable polylactic acid, and polyglycolic acid. The retaining structure includes at least one of a rough surface texture, a protrusion, a surface geometry, a bore defined in the head portion, and a through hole defined in the head portion. The retaining structure includes at least one of a bore and a through hole defined in the head portion, and a bore defined in an exterior surface of the fastener such that the bore defined in the exterior surface of the fastener intersects the at least one of the bore and the through hole defined in the head portion. The deformable portion extends into the at least one of the bore and the through hole defined in the head portion and wherein the deformable portion is exposed to the bore defined in the exterior surface of the fastener. The deformable portion includes at least one flute formed in an exterior surface of the deformable portion. The fastener also includes a spherical external surface portion disposed between the deformable portion and the bone engaging portion. The bone engaging portion includes at least one of a smooth shaft, a threaded shaft, a helical blade, a tack, a deployable talon, and an expanding element.

In another general aspect, a method of making a fastener includes forming a bone engaging portion, forming a head portion, contacting a deformable portion with the head portion, and providing a retaining structure that retains the deformable portion in contact with the head portion by a force that includes a non-frictional component.

Implementations may include one or more of the following features. For example, the deformable portion includes at least one of polyetheretherketone, polyether ketone ketone, self-reinforced polyphenylene, polyphenylsulfone, polysulfone, polyethylene, ultra high molecular weight polyethylene, a carbon composite, resorbable polylactic acid, and polyglycolic acid. Providing the retaining structure includes forming at least one of a rough surface texture, a protrusion, a surface geometry, a bore, and a through hole on the head portion of the fastener. Providing the retaining structure includes forming at least one of a bore and a through hole in the head portion, and forming a bore in an exterior surface of the fastener such that the bore in the exterior surface of the fastener intersects the at least one of the bore and the through hole formed in the head portion. The deformable portion extends into the at least one of the bore and the through hole formed in the head portion and wherein the deformable portion is exposed to the bore formed in the exterior surface of the fastener. The method also includes forming a spherical external surface portion between the deformable portion and the bone engaging portion. Forming the bone engaging portion comprises at least one of forming a smooth shaft, a threaded shaft, a helical blade, a tack, a deployable talon, and an expanding element.

In another general aspect, a fastener includes a relatively rigid portion comprising a first retaining element, and a relatively deformable portion having a second retaining element. The relatively deformable portion is received about the relatively rigid portion such that in use when the fastener is inserted into a hole in a structure, the relatively deformable portion is deformed by the structure. The first retaining element interacts with the second retaining element to limit movement of the relatively deformable portion relative to the relatively rigid portion during deformation thereof by a force that includes a non-frictional component.

Implementations may include one or more of the following features. For example, the first retaining element includes at least one of a surface depression, a surface projection, a non-circular cross sectional portion of the relatively rigid portion, a bore defined in the relatively rigid portion, and a through hole defined in the relatively rigid portion. The relatively deformable portion includes at least one of polyetheretherketone, polyether ketone ketone, self-reinforced polyphenylene, polyphenylsulfone, polysulfone, polyethylene, ultra high molecular weight polyethylene, a carbon composite, resorbable polylactic acid, and polyglycolic acid. The relatively rigid portion includes a spherical external surface portion. The relatively rigid portion includes a bone engaging portion that includes at least one of a smooth shaft, a threaded shaft, a helical blade, a tack, a deployable talon, and an expanding element.

In another general aspect, a system includes a support structure having a first bone-engaging face and a second face opposing the first face. The support structure defines a first opening in the first face, a second opening in the second face that is larger than the first opening, and an aperture extending between the first opening and the second opening. The aperture includes one or more fastener-engaging structures. The system also includes a fastener that includes a bone engaging portion, a head portion, a deformable portion that contacts the head portion, and a retaining structure that retains the deformable portion in contact with the head portion by a force that includes a non-frictional component. The deformable portion includes a material that deforms when the fastener engages the one or more fastener-engaging structures of the stabilizing structure.

Implementations may include one or more of the following features. For example, the retaining structure includes at least one of a surface depression, a surface projection, a non-circular cross sectional portion of the head portion, a bore defined in the head portion, and a through hole defined in the head portion. The deformable portion includes at least one of polyetheretherketone, polyether ketone ketone, self-reinforced polyphenylene, polyphenylsulfone, polysulfone, polyethylene, ultra-high molecular weight polyethylene, a carbon composite, resorbable polylactic acid, and polyglycolic acid. The system also includes a spherical external surface portion disposed between the deformable portion and the bone engaging portion.

In another general aspect, a fastener includes a bone engaging portion and a head portion. The head portion includes a neck portion, a shoulder proximate the neck portion, a deformable portion that contacts at least one of the neck portion and the shoulder, and a retaining structure that retains the deformable portion in contact with the at least one of the neck portion and the shoulder by a force that includes a non-frictional component. The deformable portion including a material that deforms when the fastener engages one or more fastener-engaging structures of a stabilizing structure.

The details of one or more implementations are set forth in the accompanying drawings and the description below. Other features will be apparent from the description and drawings, and from the claims.

BRIEF DESCRIPTION OF THE DRAWINGS

FIG. 8b is a partial cut-away perspective view of the polyaxial fastener of FIG. 8a.
FIG. 9b is a partial cut-away perspective view of the polyaxial fastener of FIG. 9a.

FIG. 18b is a side view of the polyaxial fastener of FIG. 18a.

DETAILED DESCRIPTION

Implementations of the disclosure provide systems that include polyaxial fasteners and bone plates and methods of using such systems. In particular, polyaxial fasteners disclosed herein may be inserted into and secured in openings of a bone plate at any one of a plurality of insertion angles to achieve a rigid construct with the bone plate.

Figure 7:
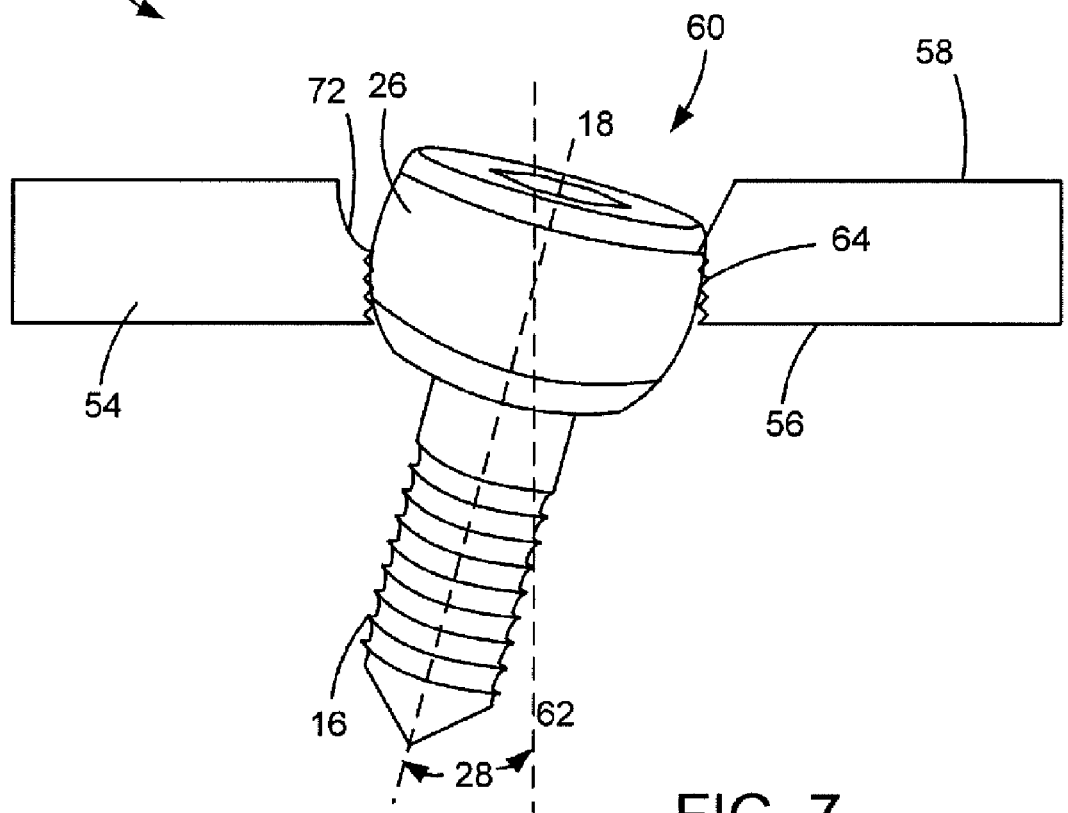
FIG. 7 is another view of the polyaxial fastener and bone plate shown in FIG. 6.
Figure 34:
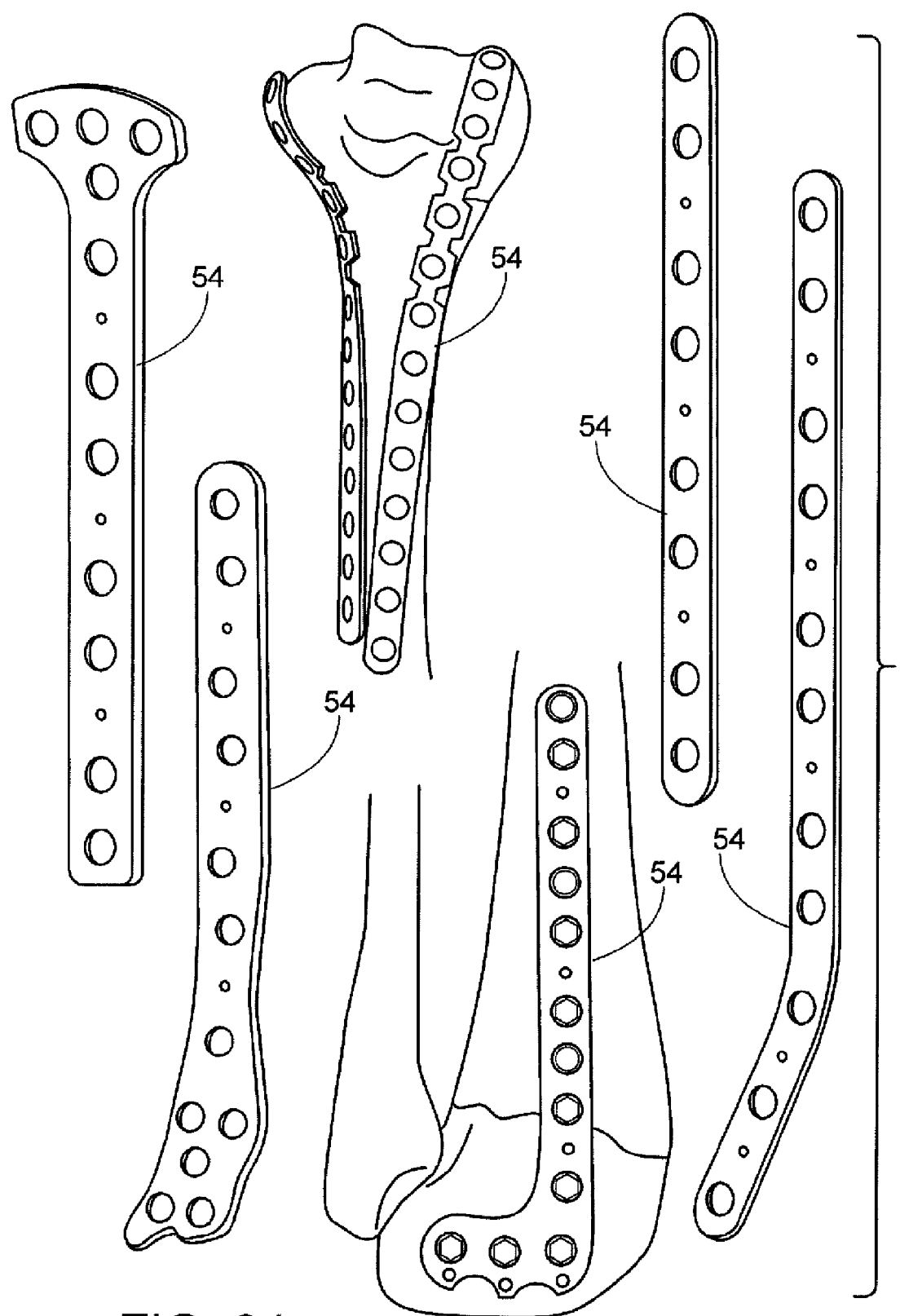
FIG. 34 includes views of bone plates.

Referring to FIG. 7, the system 10 may include any of a variety of different types of bone plates, generally denoted by reference number 54, of any shape and size. For example, bone plates 54 may be adapted to contact a femur, a distal tibia, a proximal tibia, a proximal humerus, a distal humerus, a clavicle, a fibula, an ulna, a radius, bones of the foot, and/or bones of the hand. Each bone plate 54 may be curved, contoured, straight, or flat and may be a periarticular plate or a straight plate. The bone plate 54 may have a head portion that is contoured to match a particular bone surface or a head that flares out from the shaft portion to form an L-shape, a T-shape, or a Y-shape with the shaft portion. Non-limiting examples of bone plates 54 are shown in FIG. 34.

In addition, bone plates 54 may be made of a variety of materials such as titanium, stainless steel, cobalt chrome, combinations and/or alloys thereof. Bone plates 54 may also be made of plastics. For example, the bone plate 54 can include polyetheretherketone (PEEK), carbon fiber reinforced PEEK, polyethylene, ultra high molecular weight polyethylene (UHMWPE), a carbon composite, resorbable polylactic acid (PLA), polyglycolic acid (PGA), and/or combinations of such materials may be used. The plate 54 may be formed by a combination of metal and polymer, such as a polymer plate with a threaded metal hole insert. In general, the bone plate 54 may be made of any appropriate material that has load-bearing strength while also having sufficient biocompatibility and/or bioresorbability to be implanted into a body.

Bone plates 54 may be provided with any number and type of openings in any combination. In general, the openings extend through the plate 54 from an upper surface 58 to a bone contacting surface 56 and have a central axis 62, as shown in FIGS. 6, 7, and 19-23. A variety of types of openings are described herein; however, by no means is the disclosure intended to be limited to plates having only these openings.

Some of the bone plates 54 of the system 10 include non-threaded slots 84 or openings 80 (FIG. 33) that are devoid of any structure on the inner surface 34 for engaging a fastener. Bone plates 54 may also be provided with one or more threaded openings 60 that include threads 64 on the inner surfaces 34 of the threaded openings 60. The threads 64 may include a continuous ridge or a non-continuous ridge. The threads 64 may include only a portion of a revolution, one complete revolution, multiple revolutions, a single lead, multiple leads, or any other thread feature known in the art. Moreover, the bone plates 54 can include openings 60 that include both threaded and non-threaded portions (called combination openings), such as those disclosed in U.S. Pat. No. 5,709,686 to Talos et al., the entirety of which is herein incorporated by reference.

Figure 20:
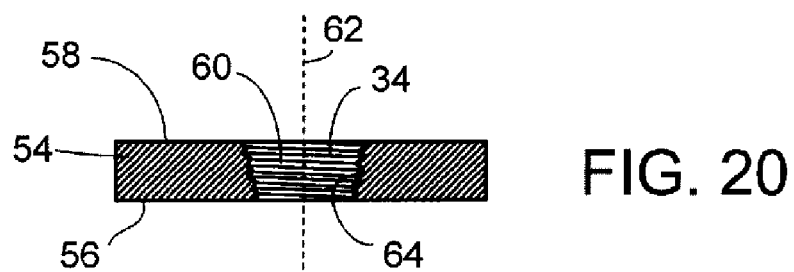
FIGS. 20-31 illustrate openings in bone plates.

FIG. 20 illustrates a threaded opening 60 having threads 64 extending continuously from the upper surface 58 to the bone contacting surface 56; however, in other implementations, the threads 64 do not extend the full distance from the upper surface 58 to the bone contacting surface 56. For example, FIGS. 26-31 illustrate threaded openings 60 having non-threaded top portions 72 proximate the upper surface 58 and threaded bottom portions 78 proximate the bone contacting surface 56. Such threaded openings 60 are described in detail in U.S. patent application Ser. No. 11/644,306, the entirety of which is hereby incorporated by reference.

Figure 24:
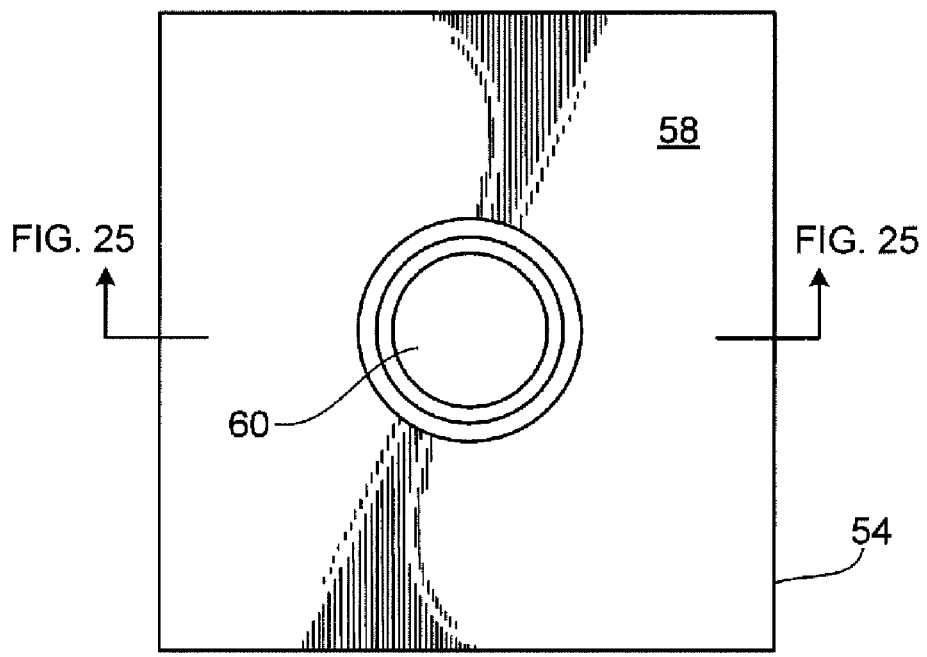
Figure 25:
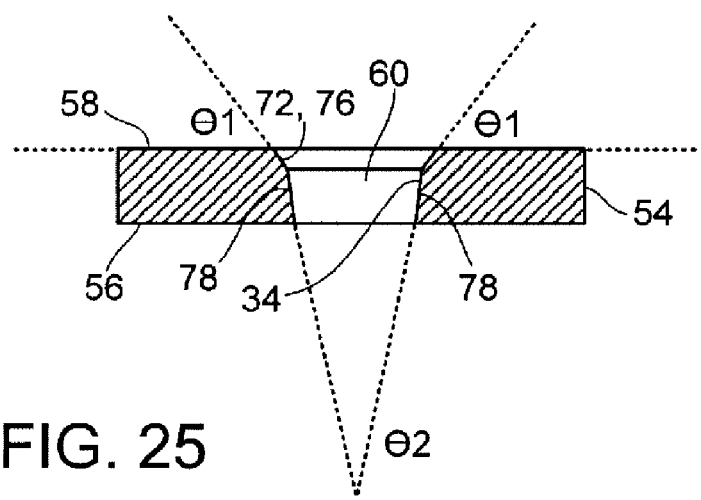
Figure 26:
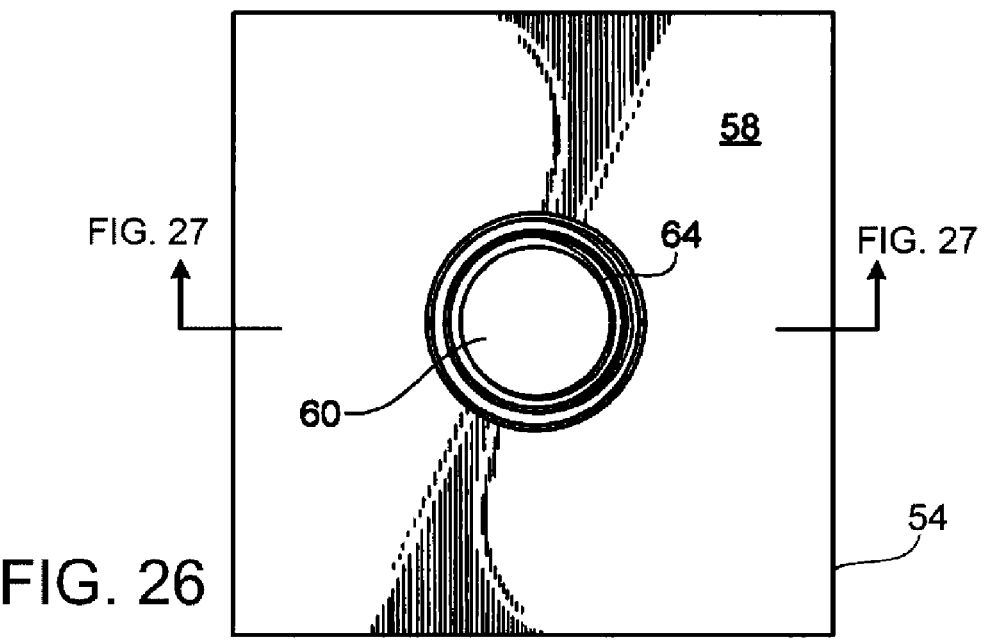
Figure 27:
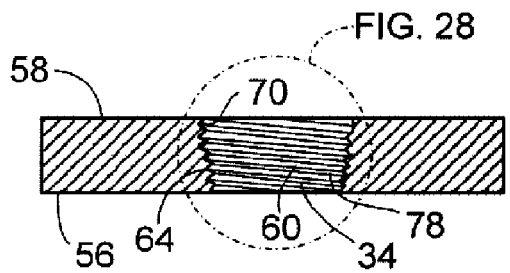
Figure 28:
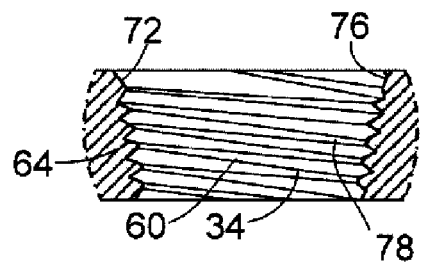

FIGS. 24-31 illustrate threaded openings 60 having a frustoconical-shaped top portion 72. FIGS. 24 and 25 show the threaded opening 60 without any threads 64 to help illustrate certain aspects of the opening 60, while FIGS. 26-28 illustrate the same threaded opening 60 with threads 64. It should be understood that the geometry of threaded opening 60 is generally the same throughout FIGS. 24-28, however.

As shown in FIGS. 24-28, the threaded opening 60 includes a top portion 72 extending downward from the upper surface 58. The top portion 72 is generally frustoconical in shape and more specifically includes a ramp 76 that extends from the upper surface 58 at an angle of θ1 relative to the plane of the upper surface 58. For example, the angle θ1 is about 52°.

Figure 29:
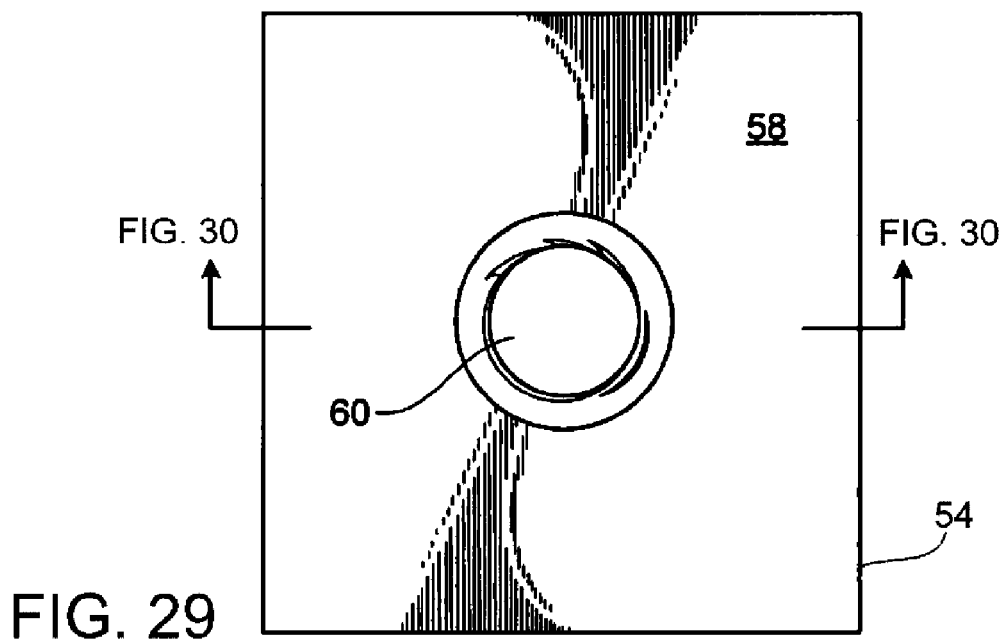
Figure 30:
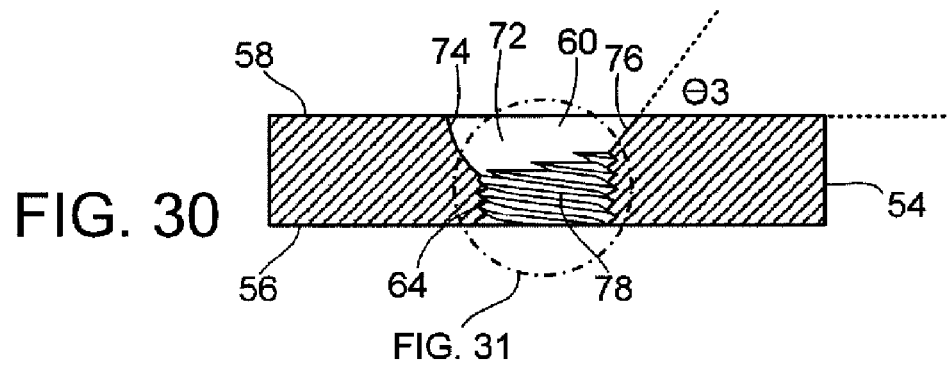
Figure 31:
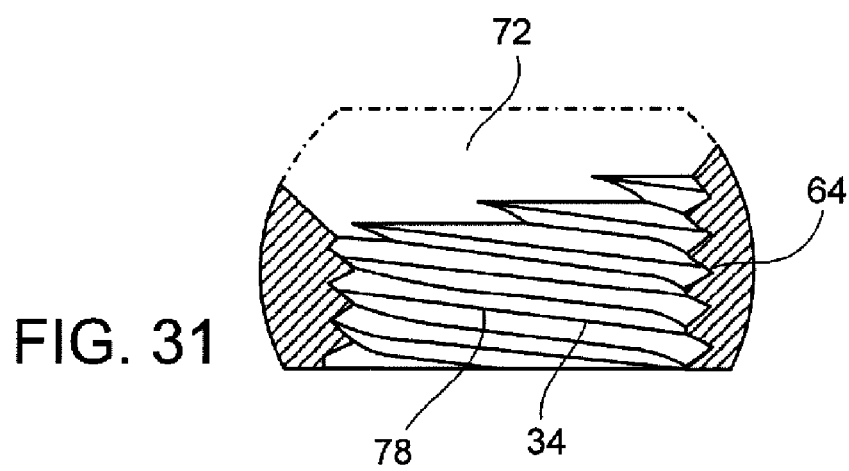

The threaded opening 60 illustrated in FIGS. 29-31 also includes a frustoconical-shaped top portion 72; however, the geometry is slightly different than the geometry of the top portion 72 shown in FIG. 25. In FIG. 30, for example, a first area of the top portion 72 includes a concave portion 74 that is generally semi-spherical in shape. A second area of the top portion includes a ramp 76 that extends from the upper surface 58 at an angle of θ3 relative to the plane of the upper surface 58. For example, the angle θ3 is about 52°.

Regardless of the precise geometry of the top portions 72 of the threaded openings 60 of FIGS. 24-31, the bottom portion 78 of threaded opening 60, which extends from the end of the top portion 72 to the bone contacting surface 56, includes threads 64. Some of the threads 64 may extend into the top portion 72 depending on the particular implementation. In general, the top portion 72 is not completely threaded. As shown in FIG. 25, the bottom portion 78 is tapered. The included angle θ2 of the taper of the bottom portion 78 may be less than about 30°, including 0° (i.e., no taper at all). The larger the included angle θ2, the larger that threaded opening 60 must be at the upper surface 58. Increasing the size of the threaded opening 60 may compromise the strength of the bone plate 54 if the included angle θ2 is much larger than about 30°. In an example implementation, the included angle θ2 is about 20°.

Bone plate 54 can have one or more of a variety of openings 60 with different geometries, and the applicability of the disclosure is not limited to the specific openings shown in the figures. For example, the opening 92 of FIG. 23, has an inner surface 34 with features other than the threads 64 for engaging the head 14 of a polyaxial fastener 12. For example, the opening 92 includes fins 70 that extend inwardly into the opening 92. Such finned openings 92 are described in detail in U.S. patent application Ser. No. 11/996,795, the entirety of which is hereby incorporated by reference.

Figure 21:
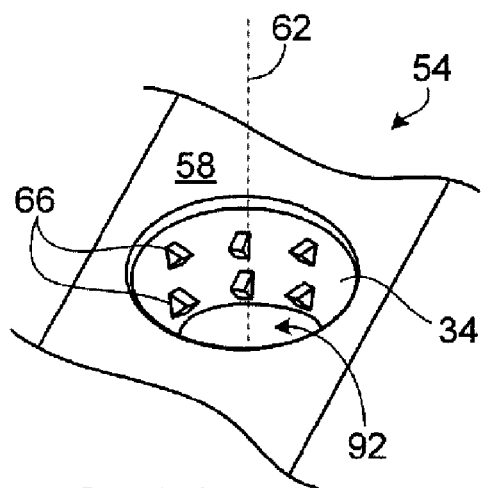
Figure 22:
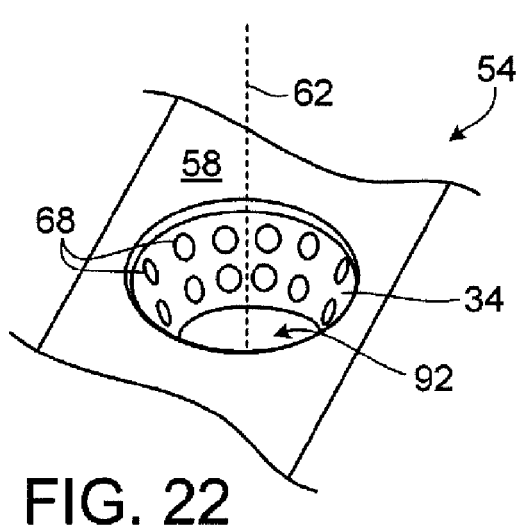
Figure 23:
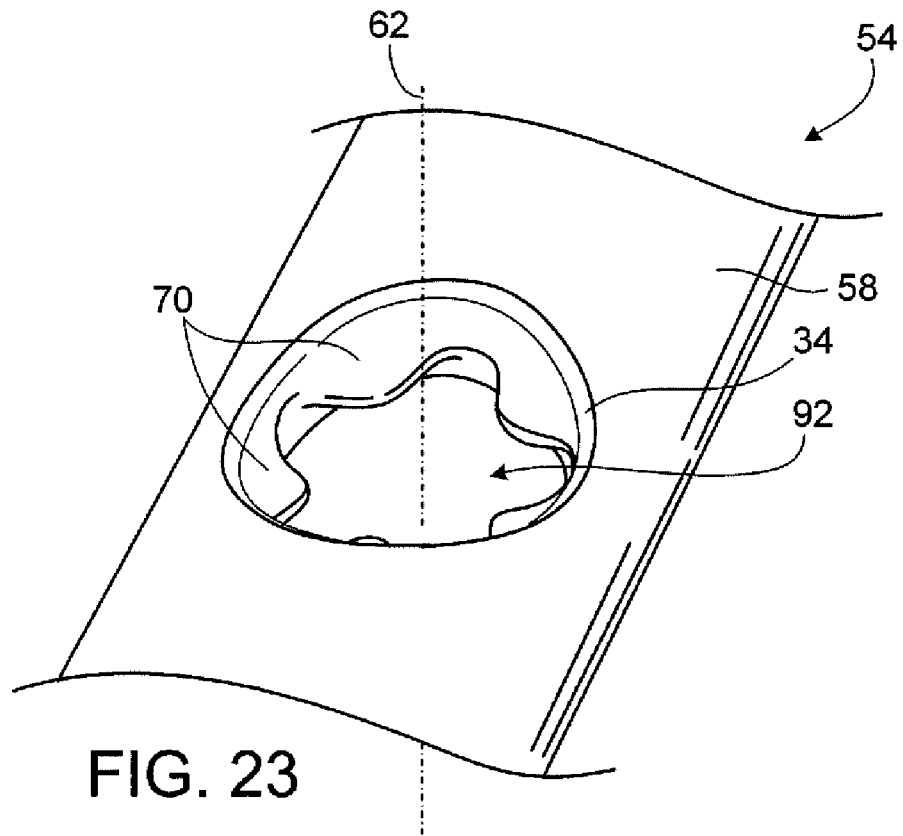

Alternatively, free-standing geometrical protrusions may be provided on the inner surface 34 of the opening 92. For example, and not by way of limitation, FIGS. 21 and 22 show discontinuous ridges 66 or bumps 68, respectively, that extend inwardly from the inner surface 34 of the opening 92. In general the inner surface 34 of the opening 92 may be provided with any feature, protrusion, or combination of features that can grasp and secure the polyaxial fasteners 12 described herein. For ease of discussion, the polyaxial fasteners 12 are described herein in use with threaded openings 60.

The polyaxial fasteners 12, as shown in FIGS. 1-8, generally have a bone engaging portion, such as a shaft 16, a head portion 14, a deformable portion 26, and a longitudinal axis 18 that extends from the tip 20 of the shaft 16 to the head 14 of the polyaxial fastener 12. The shaft 16 may be threaded or otherwise configured to engage bone. The shaft 16 may be fully threaded, partially threaded, include a helical blade, and/or may include one or more tacks, deployable talons, expanding elements, or other bone engagement structure. Any feature that allows shaft 16 to engage bone is considered to be within the scope of this disclosure and may be referred to generally as a threaded shaft 16 for the sake of convenience. Alternatively, the shaft 16 is not threaded, and the polyaxial fastener 12 takes the form of a peg or a pin. A non-threaded fastener 12 may be useful in certain procedures where, for example, the main goal is to prevent tilting of a bone segment, or in procedures where there is little or no risk of the polyaxial fastener 12 pulling out from the bone, and hence there is little or no need for the shaft 16 to be threaded or otherwise configured to engage bone to limit extraction of the fastener 12. The tip 20 of shaft 16 may be a self-tapping or a self-drilling tip. Additionally, the fastener 12 may be cannulated, whereby the shaft 16 is hollow to allow the fastener 12 to be mounted on a guide wire during insertion of the fastener 12 into bone.

In general, the polyaxial fasteners 12 described herein have a bore 22 formed in an exterior surface of the head 14 that receives a driver or other instrument that can be used to position the polyaxial fastener 12. The bore 22 may be any size and shape. For example, the bore 22 has a hexagonal configuration to receive a corresponding hexagonal driver. Other options include a Phillips screw head, a slotted head, a star configuration, a Torx configuration, or any other appropriate configuration that can cooperate with a driver to place polyaxial fastener 12.

FIGS. 1-11 illustrate embodiments of polyaxial fasteners 12 with a deformable portion 26 on the head 14 of the fasteners 12. In the embodiments shown in FIGS. 1-7, the deformable portion 26 extends around the circumference of the head 14 and is defined by a bottom portion 32. Thus, the deformable portion 26 does not cover the entire head 14. As illustrated in FIGS. 8-11, however, the deformable portion 26 may alternatively cover approximately the entirety of the head 14. In still other embodiments, the deformable portion 26 extends along only a portion or portions of the circumference of head 14 and may be provided at other locations on the head 14. Regardless of the specific geometry of the deformable portion 26, the deformable portion 26 has the same basic use as described below.

Figure 6:
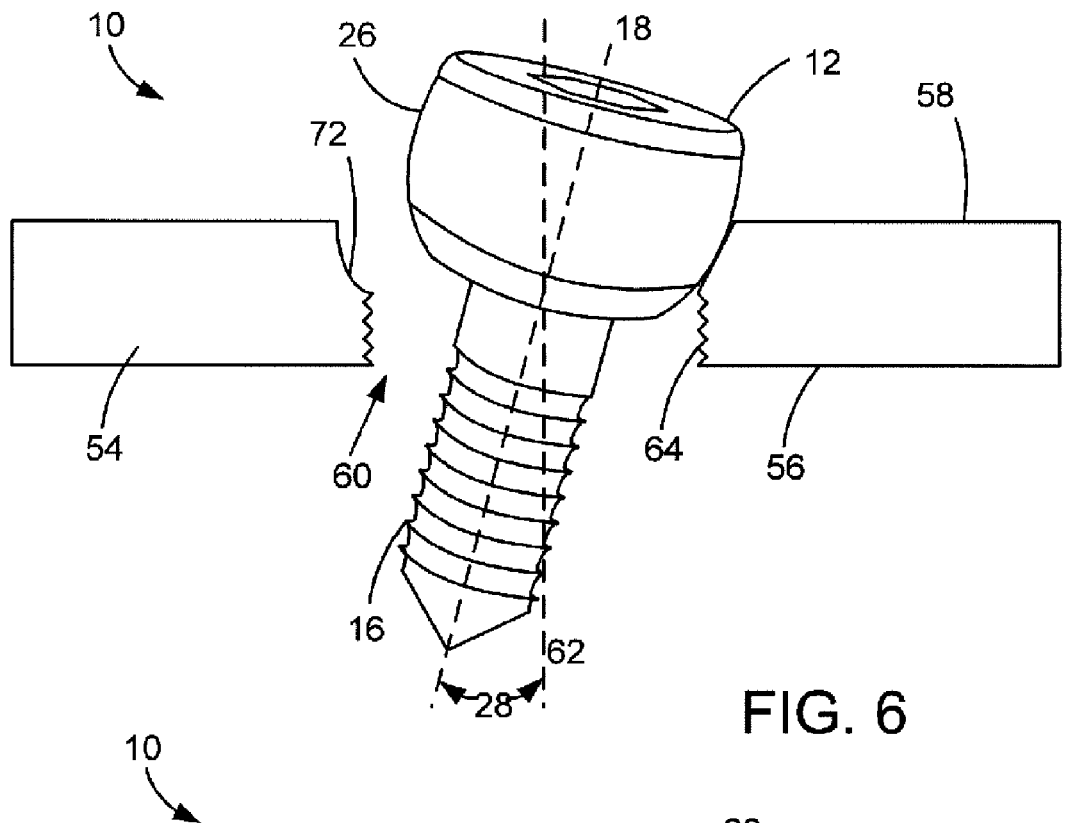
FIG. 6 is a partial cut-away perspective view of the polyaxial fastener of FIG. 1, inserted in an opening of a bone plate.

In one example, the polyaxial fastener 12 is inserted into a threaded opening 60, and torque is applied to the fastener 12 (via bore 22) to drive the fastener 12 into the bone. As the polyaxial fastener 12 is driven further into the threaded opening 60, the deformable portion 26 approaches and eventually comes into contact with the threads 64 within the threaded opening 60, as shown in FIG. 6. The threads 64 within the threaded opening 60 cut into and deform the deformable portion 26, as shown in FIG. 7. Engagement of the deformable portion 26 of the locking the polyaxial fastener 12 with the threaded opening 60 forms a secure fit between the polyaxial fastener 12 and the bone plate 54.

The polyaxial fastener 12 provides the benefits of a locking screw without the associated drawbacks. Particularly, the polyaxial fastener 12 can be locked into the threaded opening 60 by the threads 54 at a desired angular orientation of the longitudinal axis 18 of the fastener 12 relative to the central axis 62 of the opening 60. Unlike traditional locking screws, the fastener 12 provides for polyaxial fixation in that the fastener 12 may be inserted and fixed within the threaded opening 60 at any one of a plurality of insertion angles 28 (i.e., the angle between the central axis 62 of the threaded opening 60 and the longitudinal axis 18 of the polyaxial fastener 12), as shown in FIGS. 6 and 7. For example, the insertion angle 28 may range from 0° to 30° in any direction. The polyaxial fastener 12 need not be inserted into the threaded opening 60 at a precise, pre-determined angle to ensure engagement between the threads 64 of the threaded opening 60 and the head 14 of the fastener 12 because the head 14 of the fastener 12 does not include pre-formed threads. Rather, the head 14 includes the deformable portion 26, which is configured to engage the threads 64 of the opening 60 when the fastener 12 is inserted in the opening 60 at the insertion angle 28.

The deformable portion 26 is formed from a biocompatible and/or bioresorbable material that has sufficient strength to secure the polyaxial fastener 12 in place within the threaded opening 60 when inserted at the insertion angle 28 by interaction with the threads 64. The deformable portion 26 must also be sufficiently deformable that upon the application of force, the threads 64 cut into and deform the deformable portion 26 as described above. Suitable materials from which the deformable portion 26 can be formed include polymeric materials such as, but not limited to, polyetheretherketone (PEEK), polyether ketone ketone (PEKK), self-reinforced polyphenylene (SRP), polyphenylsulfone (PPSU), polysulfone (PSU), polyethylene, ultra high molecular weight polyethylene (UHMWPE), a carbon composite, resorbable polylactic acid (PLA), polyglycolic acid (PGA), and/or combinations of such materials. Fillers, such as carbon fibers or glass beads, may be incorporated into the polymeric materials of the deformable portion 26 to enhance the strength of the deformable portion 26 made from such materials. In general, the deformable portion 26 is made of a material that is softer, i.e., has a lower yield strength, than the material defining the threaded opening 60 on a bone plate 54. For example, the deformable portion 26 can be formed from PEEK-Optima LT3, manufactured by Invibio Inc., of 300 Conshohocken State Road, West Conshohocken, Pa. 19428, USA.

The polyaxial fasteners 12 may be manufactured by one or more of a variety of methods and/or using one or more of a variety of materials. For example, the head 14 may be, but does not have to be, unitary with the shaft 16, such that the head 14 and the shaft 16 may be made from a single piece of material. Suitable materials include, but are not limited to, metallic materials such as titanium, stainless steel, cobalt chrome, and/or combinations or alloys thereof. Additionally, the polyaxial fasteners 12 may be made from polymeric materials, such as, but not limited to, polyetheretherketone (PEEK), polyether ketone ketone (PEKK), carbon-reinforced PEEK, self-reinforced polyphenylene (SRP), polyphenylsulfone (PPSU), polysulfone (PSU), polyethylene, ultra high molecular weight polyethylene (UHMWPE), a carbon composite, resorbable polylactic acid (PLA), polyglycolic acid (PGA), and/or combinations of such polymeric materials.

Figure 2:
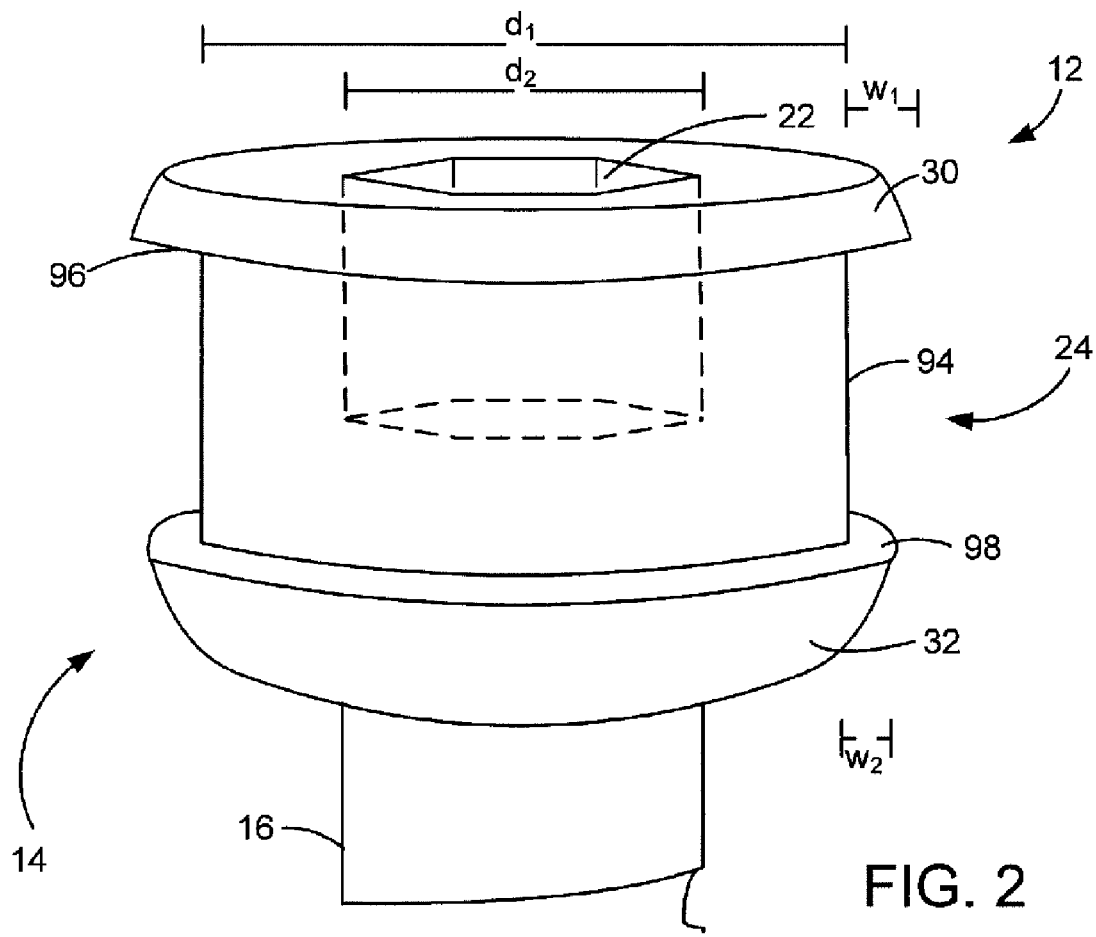
FIG. 2 is a partial perspective view of the head of the polyaxial fastener shown in FIG. 1.
Figure 3:
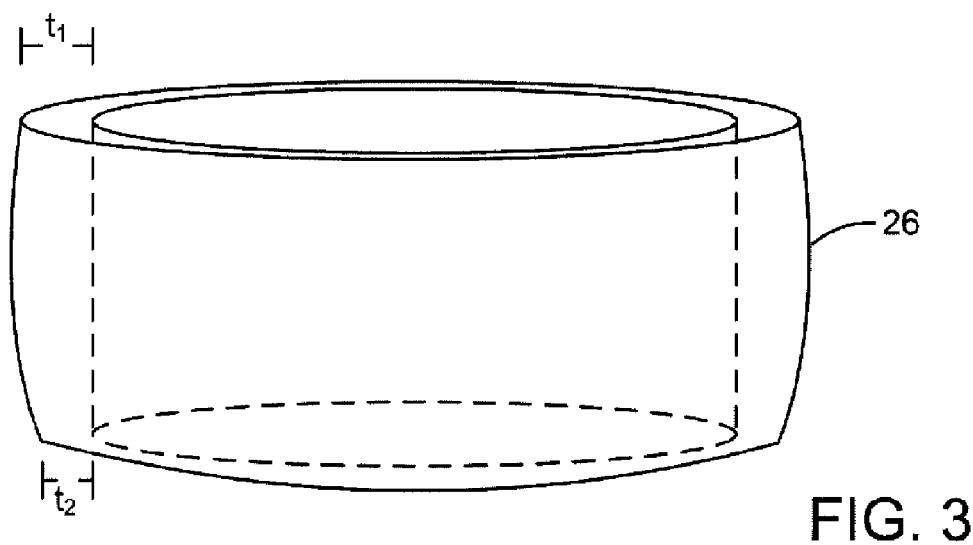
FIG. 3 is a perspective view of a deformable portion of the polyaxial fastener shown in FIG. 1.

As shown in FIG. 2, at least one recess 24 is provided in the head 14 to accommodate the deformable portion 26. The recess 24 may be formed around all or a portion of the circumference of the head 14. In the illustrated non-limiting example of FIG. 2, the recess 24 is an annular groove that extends entirely around the head 14. Again, however, more than one recess 24 may be provided and a recess 24 need not extend continuously around the head 14. The recess 24 may be formed in a variety of ways. For example, a lathe may be used to remove material from the head 14 to form the recess 24. Alternatively, the polyaxial fastener 12 may be molded to include the recess 24. The deformable portion 26 is then provided at least partially within the recess 24 by a variety of techniques. In some examples, the deformable portion 26 is molded onto the head 14 such that the deformable portion extends at least partially into the recess 24. After forming the deformable portion 26, a lathe may be used to remove excess material and thereby to form the deformable material into a desired shape of the deformable portion 26, one of which is illustrated in FIG. 3. In other examples, a pre-formed deformable portion 26 may be fitted into the recess 24 by known techniques, such as assembly, adhering, shrink-fitting, or any appropriate manufacturing method.

Figure 1:
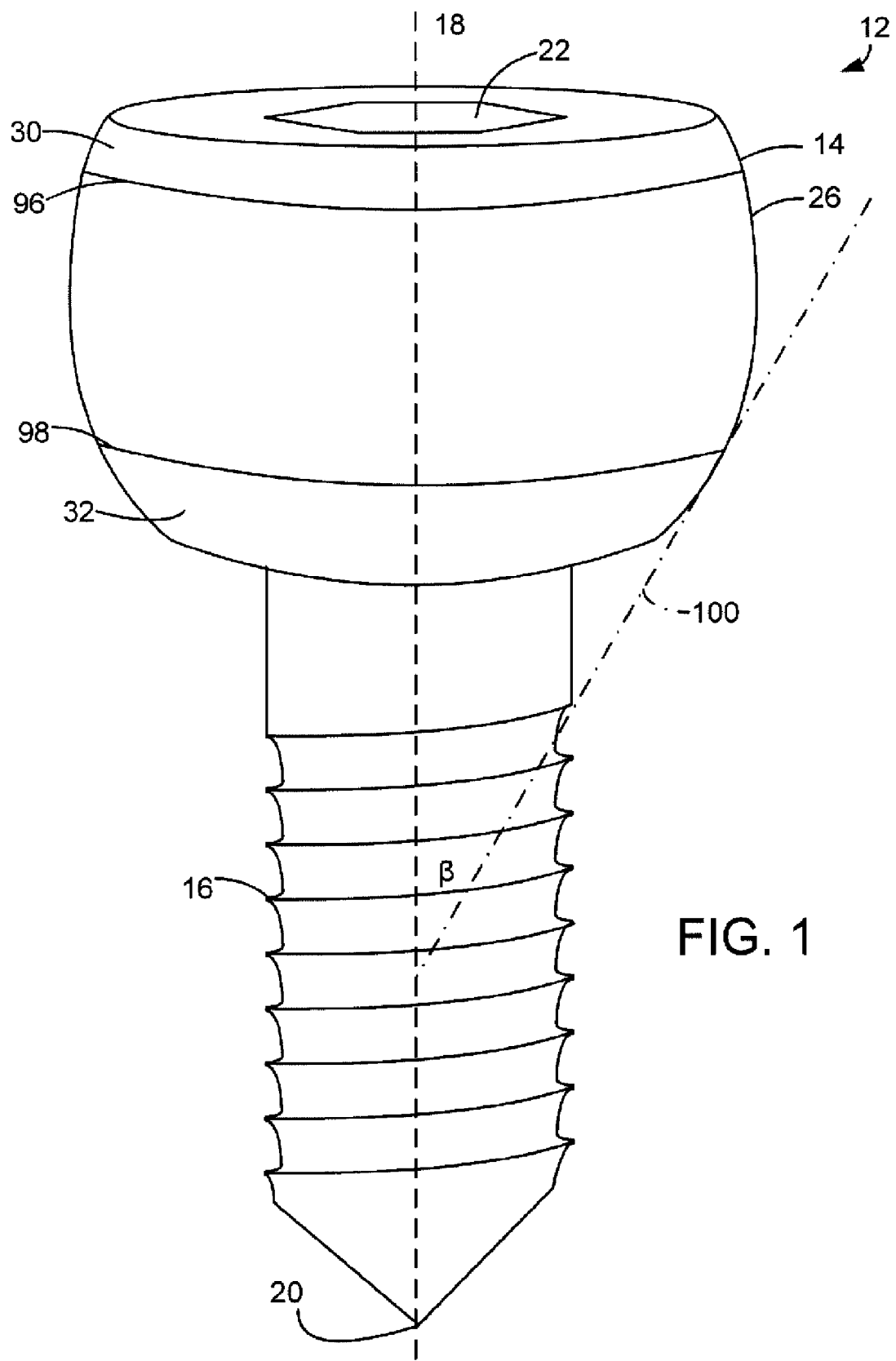
FIG. 1 is a perspective view of a polyaxial fastener.

As shown in FIGS. 1-3, the head 14 includes a top portion or shoulder 30, a neck 94, and a bottom portion or shoulder 32 that collectively define the recess 24. The top portion 30 defines the top wall 96 of the recess 24 and the bottom portion 32 defines the bottom wall 98 of the recess 24. The bottom portion 32 may have any one of a variety of curved or angular geometries, including spherical, conical, and paraboloid, among others. As best seen in FIG. 1, a tangent line 100 to the bottom portion 32 represents the point of contact between the bottom portion 32 of the head 14 and the threaded opening 60. The tangent line 100 intersects with, and forms an angle β relative to, the longitudinal axis 18 of the fastener 12. The bottom portion 32 is dimensioned so that the angle β is between approximately 20° and 90°, inclusive. When the angle β is approximately 90°, there is generally no bottom portion 32 and the deformable portion 26 generally extends to a location where the shaft 16 intersects with the head 14.

The bore 22 extends into the top portion 30 and the neck 94 of head 14. The neck 94 may have any suitable diameter $d_1$, provided that there is sufficient amount of material to form the bore 22 and a wall between the bore 22 and the outer surface of the neck 94. In other words, the diameter $d_1$ of the neck 94 is constrained by the diameter $d_2$ of the bore 22, and/or the diameter of the bore $d_2$ is constrained by the diameter $d_1$ of the neck 94, such that the wall of the neck 94 has a thickness that is sufficient to prevent or limit distortion or tearing when a surgeon or other user drives the polyaxial fastener 12 into bone using a driving tool engaged with the bore 22. In some implementations, the head 14 can be formed from an end portion of a the shaft 16 that includes a structure for engaging a driver, and the diameter d1 can be substantially the same size as a diameter of a portion of the shaft 16 that engages the bone. The recess 14 may be omitted, or may be formed by removing material from the non-threaded portion of the shaft, and the deformable portion 26 can be provided on the head 14 as described elsewhere in this disclosure, for example.

The recess 24 illustrated in FIGS. 1-3 is formed as a circular cylinder where the diameter d1 of the neck 94 is consistent throughout its height and the walls of the neck 94 are generally parallel with the longitudinal axis 18 of the polyaxial fastener 12. The top wall 96 of the recess 24 has a width $w_1$ that is greater than the width $w_2$ of the bottom wall 98 and the deformable portion 26 has a thickness $t_1$ proximate the top portion 30 of the head 14 that is greater than a thickness $t_2$ proximate the bottom portion 32. The width $w_1$ is selected to provide a top wall 96 that retains the deformable portion 26 within the recess 24 during insertion of the fastener 12 in the threaded opening 60, during which an axial force is applied to the deformable portion relative to the head 14. Similarly, the width $w_2$ is selected to provide a bottom wall 98 that retains the deformable portion within the recess 24 in use to limit the fastener 12 backing out of the opening 60.

Figure 4:
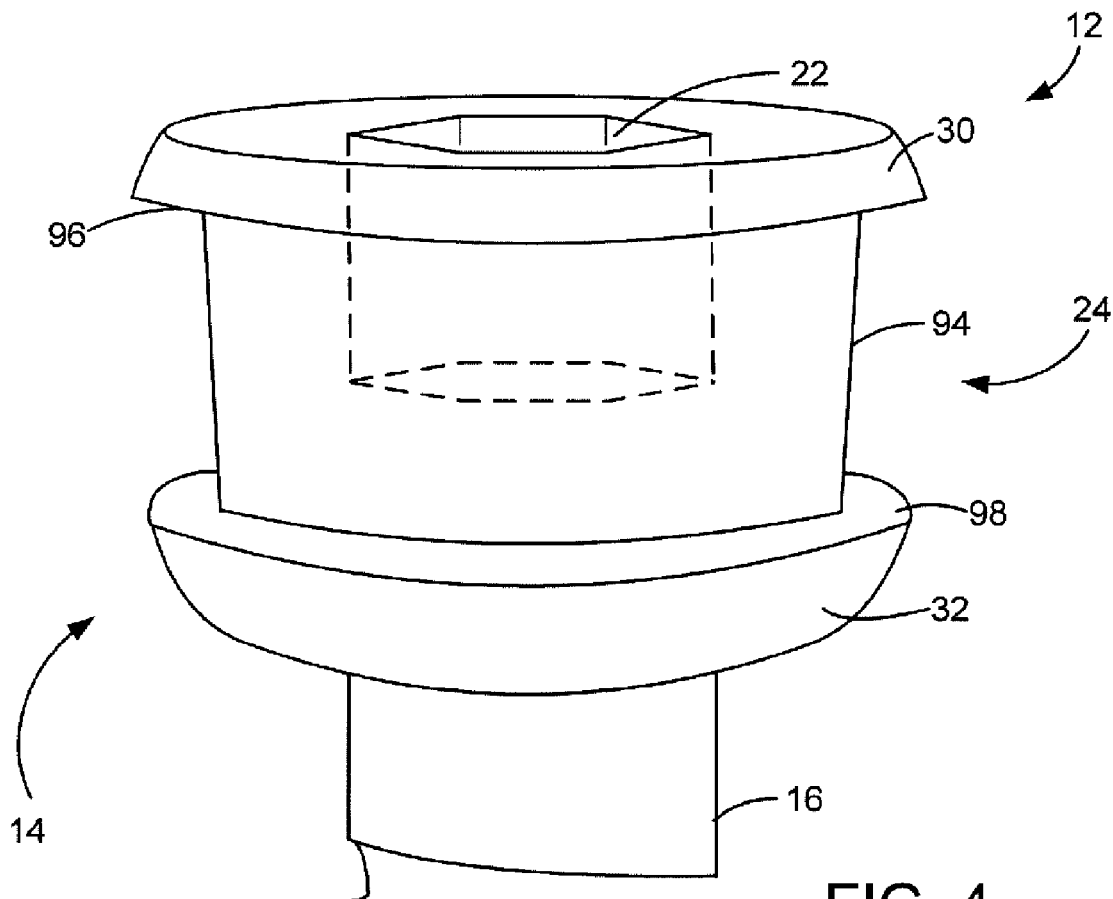
FIG. 4 is a partial perspective view of another head of a polyaxial fastener.
Figure 5:
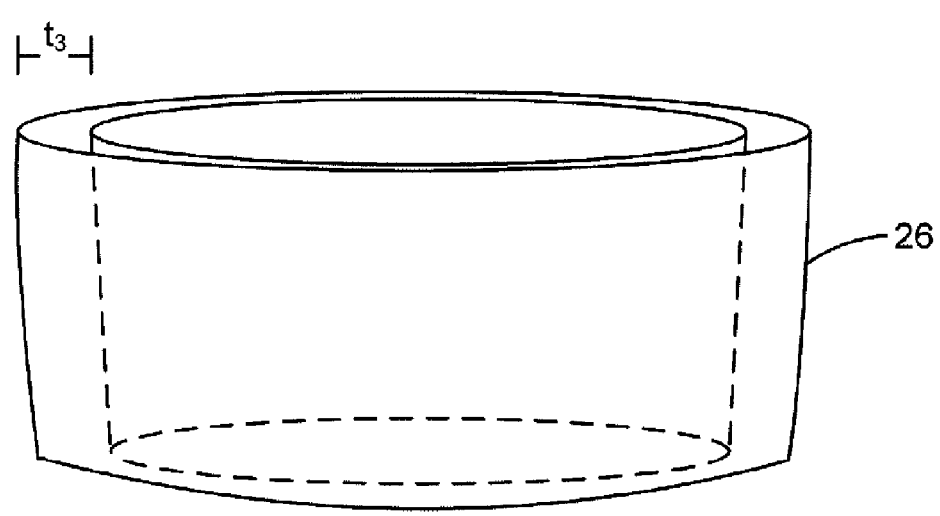
FIG. 5 is a perspective view of another deformable portion of the polyaxial fastener.

In other examples, as shown in FIGS. 4 and 5, the neck 94 is tapered or otherwise shaped so that the diameter of the neck 94 varies along its height. In FIGS. 4 and 5, the neck 94 slopes downwardly away from the top portion 30 towards the bottom portion 32. In some examples, the slope of the neck 94 may match a desired shape of the outer perimeter of the head 14 so that the deformable portion 26 positioned in the recess 24 has a constant thickness $t_3$ throughout its height.

In general, the deformable portion 26 may have any thickness such that the deformable portion 26 contacts the threads 64 in the threaded opening 60 when inserted in the opening 60 to facilitate locking of the polyaxial fastener 12 in the threaded opening 60. The thickness of the deformable portion 26 can vary depending on the size of the threads 64, the size of the threaded opening 60 into which the fastener 12 is intended for insertion, the diameter $d_1$ of the neck 94 and the widths $w_1$ and $w_2$ of the top wall 96 and the bottom wall 98. In general, a deformable portion 26 of a larger fastener 12 will have a greater thickness than a deformable portion 26 of a smaller fastener 12 of a similar design. However, the thicknesses of a deformable portion 26 of between approximately 0.25 mm to approximately 4 mm is suitable for most applications. The deformable portion 26 is preferably thick enough to ensure that the threads 64 of the threaded opening 60 do not cut entirely through the deformable portion 26, such that chunks or pieces of the deformable portion 26 are not formed by separating from the fastener 12 due to interaction with the threads 64.

The head 14 of the fastener 12 may have any profile suitable for the intended interaction with the threaded opening 60. Conical-shaped profiles, spherical profiles, and paraboloid profiles are suitable, and can be used with openings 60 that are conical or that have frustoconical top portions. Moreover and as discussed above, the size of the deformable portion 26 exposed on the head 14 of the fastener 12 may also be selected according to a particular application in which the fastener 12 is intended to be used. For example, FIGS. 1-5 illustrate fasteners 12 that have deformable portions 26 that do not encompass the entirety of the outside surface of the head 14. A bottom portion 32 of the head 14 remains exposed and the deformable portion 26 is formed in the shape of a band that extends around the periphery of the head 14 above the bottom portion 32. As shown, the fastener 12 has a spherical profile. The fastener 12 may be used in any type of opening, and is particularly useful to achieve both compression and fixation. More specifically, the fastener 12 has an exposed bottom portion 32 may be used with a threaded opening 60 that includes a compression slope, such as, but not limited to, the threaded openings 60 shown in FIGS. 24-31 that has a frustoconical top portion 72.

In use, and as illustrated in FIG. 6, the polyaxial fastener 12 is inserted into a threaded opening 60 and the bottom portion 32 comes into contact with the frustoconical top portion 72 of threaded opening 60. As the fastener 12 is further driven into a bone, the bottom portion 32 of the head 14 rides along and bears against the frustoconical top portion 72. The polyaxial fastener 12 pushes the bone plate 54 in a particular direction, for example a lateral direction, as the curved contour of the bottom portion 32 contacts and rides along the frustoconical top portion 72 of threaded opening 60, as illustrated in FIG. 7. By moving the bone plate 54, the underlying bone fragments and tissue move relative to the plate 54 to reduce a fracture. Movement of the bone relative to the plate 54 may be further facilitated by the coefficient of friction of the bottom portion 32. In some embodiments, the bottom portion 32 may be formed from a material having a low coefficient of friction to facilitate movement along the frustoconical top portion 72. A surgeon or other user may thus move the bone plate 54 into a desired position using the contoured bottom portion 32. Then the surgeon or other user may fixedly secure the polyaxial fastener 12 in a desired position by applying torque to the fastener 12 and causing the deformable portion 26 to come into contact with and be deformed by the threads 64 as described above.

Figure 8A:
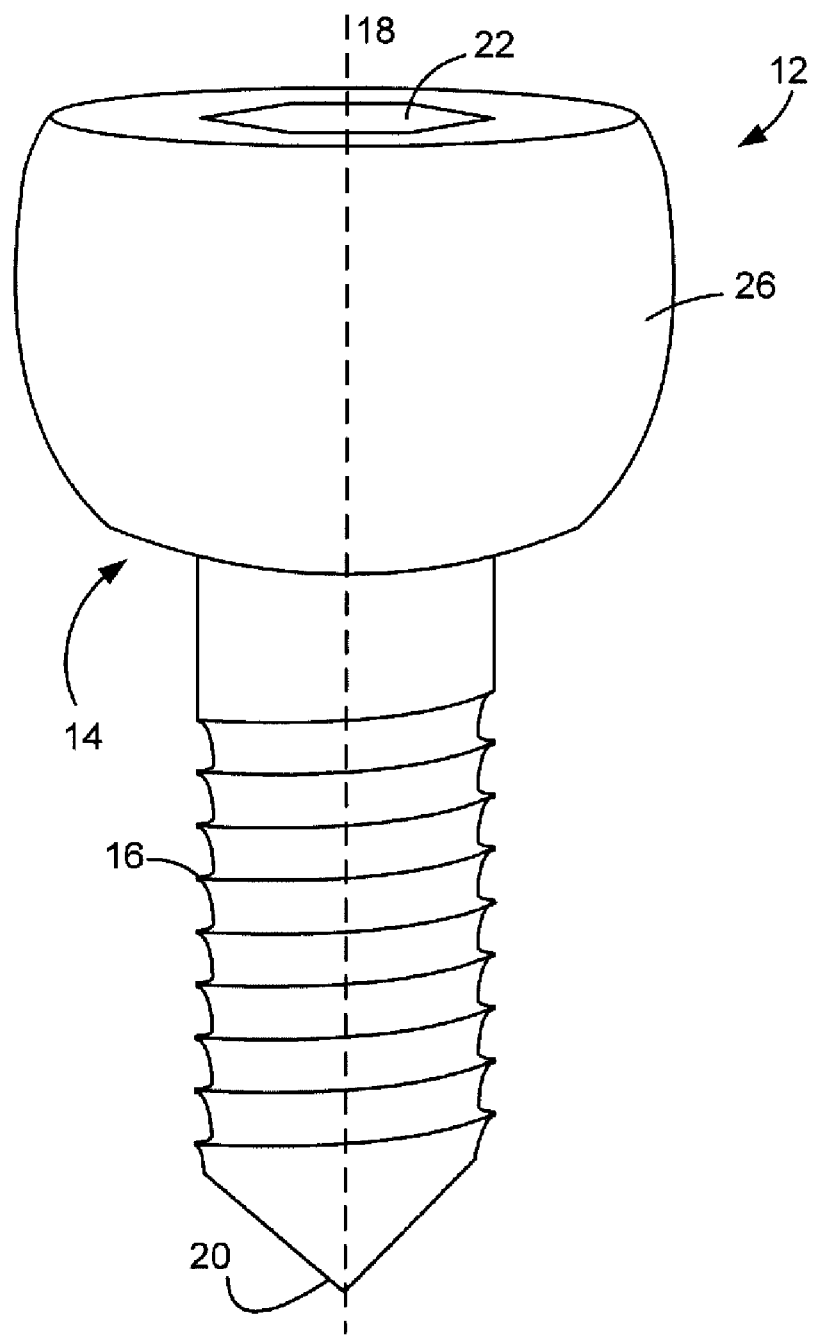
FIG. 8a is a perspective view of a polyaxial fastener.
Figure 8B:
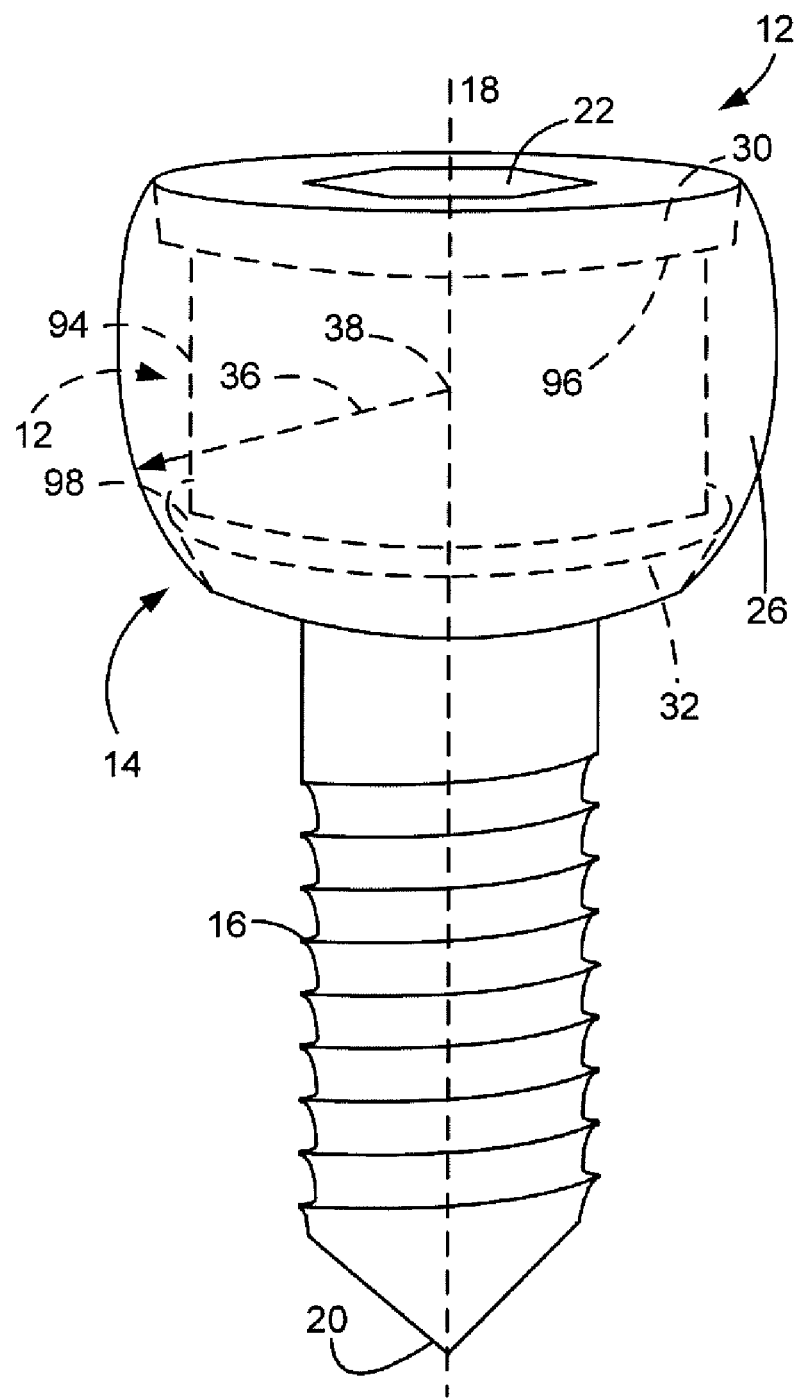
Figure 9A:
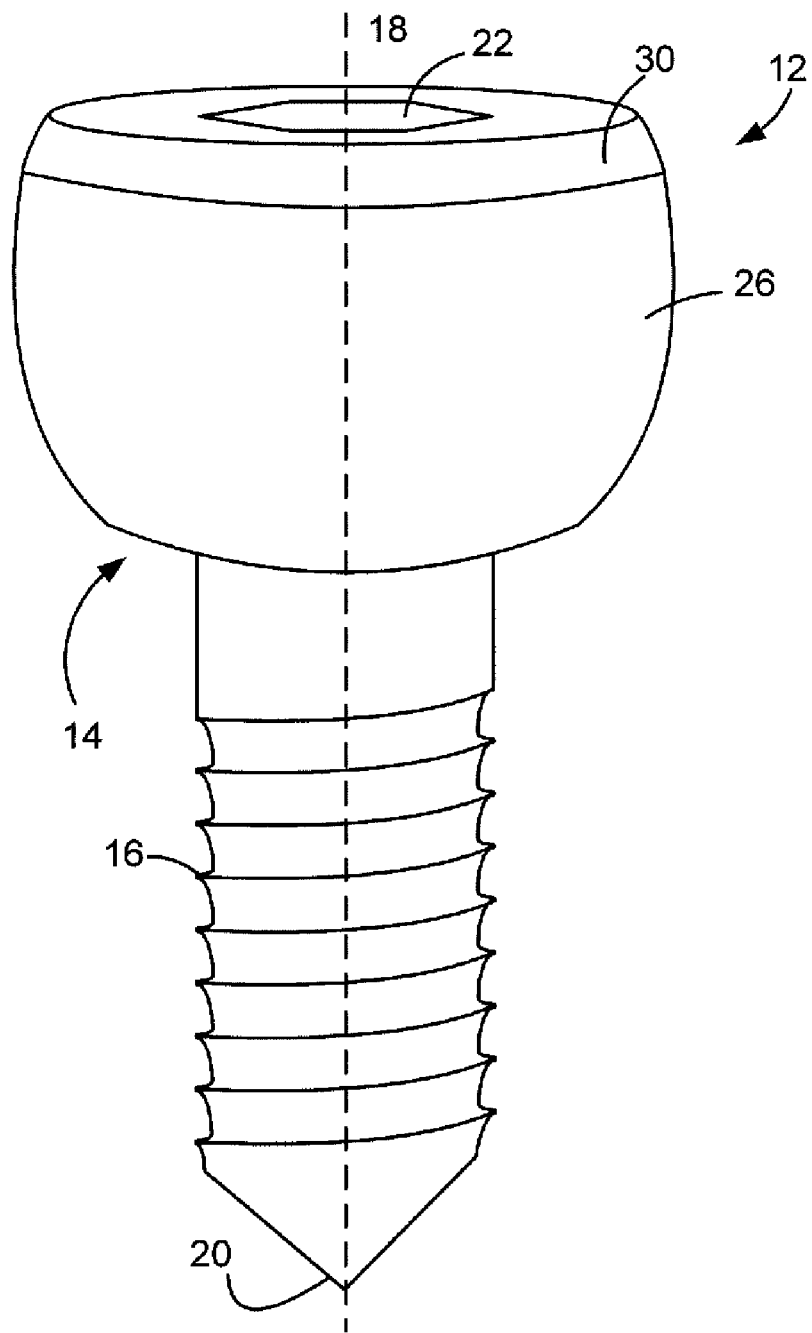
FIG. 9a is a perspective view of a polyaxial fastener.
Figure 9B:
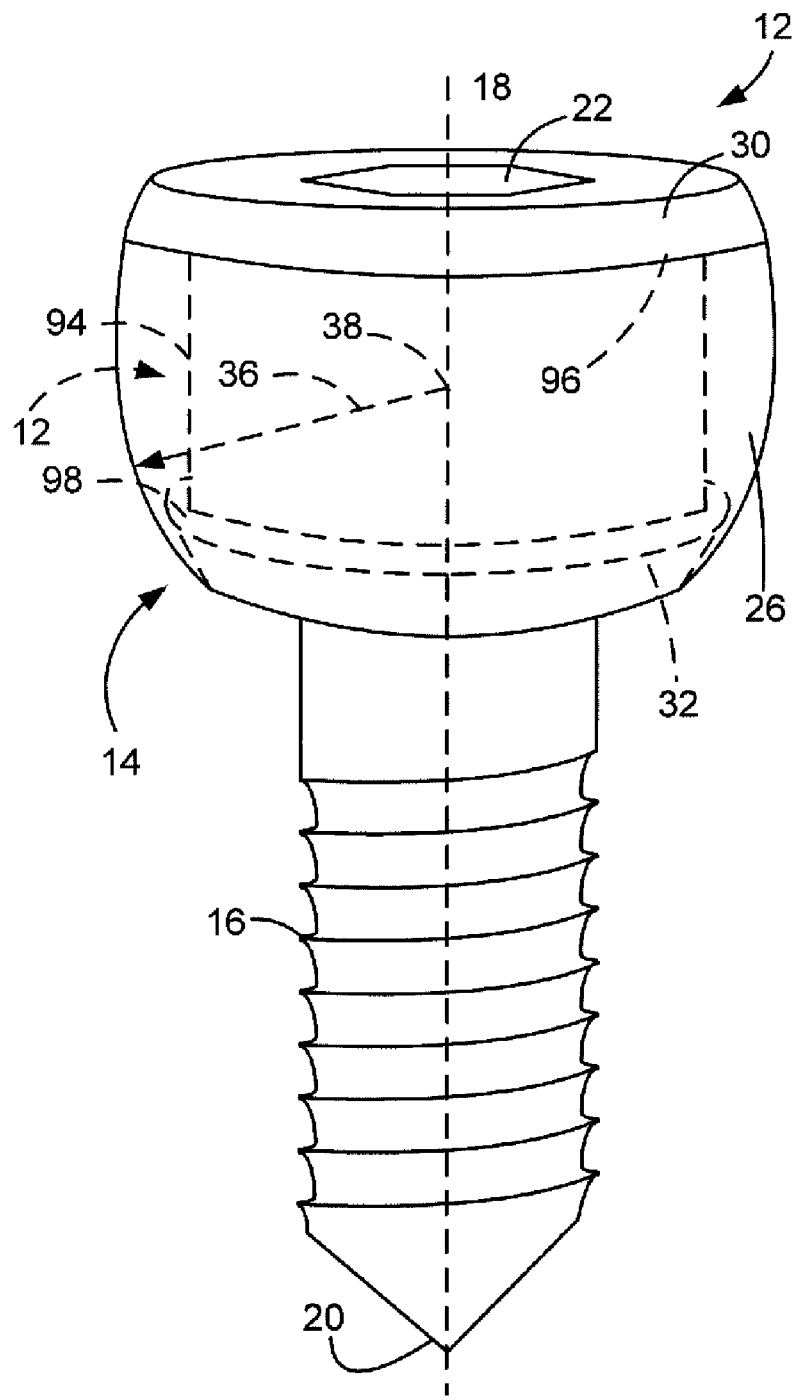

The fasteners 12 shown in FIGS. 8a, 8b, 9a, and 9b have deformable portions 26 that extend around the entirety of the periphery of the head 14 and form a substantially spherical profile. In FIGS. 8a and 8b, the deformable portion 26 extends from the top portion 30 of the head 14 to the bottom portion 32 of the head 14. In FIGS. 9a and 9b, however, the deformable portion 26 does not extend all the way to the top portion 30 of the head 14, but rather stops short just beneath the top portion 30. Again, however, the amount of deformable portion 26 exposed on the head 14 may be tailored as desired.

The head 14 has a radius 36 and a center 38 as shown in the figures. The center 38 lies on the longitudinal axis 18 of the polyaxial fastener 12. While not required, it may be preferable to form the deformable portion 26 so that the radius 36 of the head 14 is constant throughout the deformable portion 26. This geometry of the center 38 and the radius 36 ensures a secure fit of the polyaxial fastener 12 within the threaded opening 60 by providing for an approximately equal amount of thread interference 40 around the circumference of the head 14 at any insertion angle of the fastener 12. The thread interference 40 may be seen in FIGS. 10 and 11, and refers to the depth at which the threads 64 within threaded opening 60 cut into and deform the deformable portion 26. Equal thread interference 40 helps ensure a secure fit and an approximately equal amount of pull-out strength around the circumference of the head 14 at all insertion angles of the fastener 12.

Figure 12:
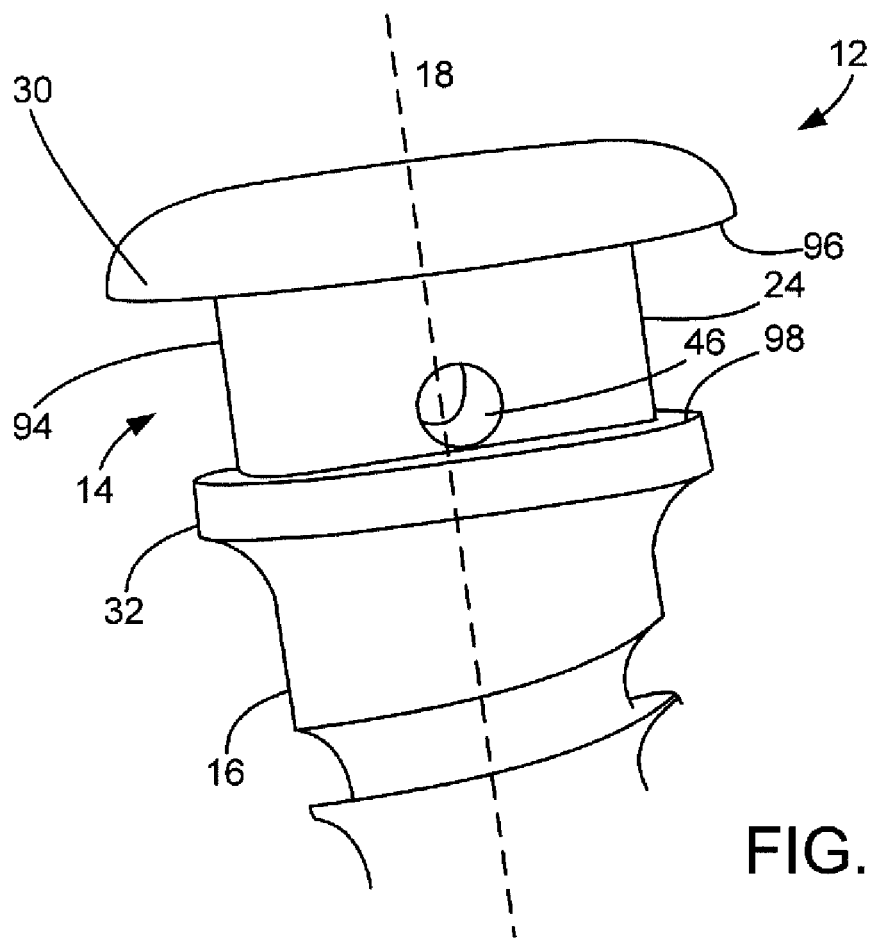
FIG. 12 is a perspective view of a polyaxial fastener with an anchor hole through the fastener head.
Figure 13:
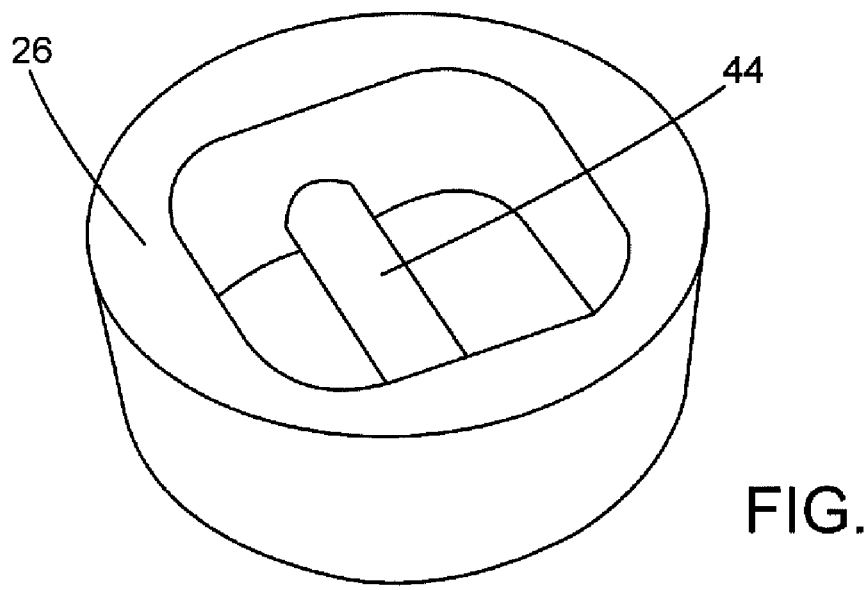
FIG. 13 is a perspective view of the deformable portion formed on the head of the polyaxial fastener shown in FIG. 12.

As discussed above, the deformable portion 26 is positioned in at least one recess 24 defined on the head 14 of the fastener 12. Movement between the deformable portion 26 and the head 24 is limited by the top wall 96, the bottom wall 98 (if included), and/or friction between the neck 94, the upper wall 96, and/or the bottom wall 98 and the surfaces of the deformable portion 26. Particularly to limit rotation of the deformable portion about the neck 94 during insertion of the fastener 12 into bone through an opening of a bone plate or other support structure, the geometry of the head 14 may be, but does not have to be, configured to enhance retention of the deformable portion 26 on the head 14. For example, while the neck 94 illustrated in the figures has a circular cross-section, the neck 94 can have other cross-sectional shapes (e.g., square, triangle, hexagon, octagon, etc.) that help prevent the deformable portion 26 from rotating in the recess 24. For example, as shown in FIGS. 12 and 13, the neck 94 may have a rounded polygonal cross-sectional shape. The non-circular cross-sectional shape of the neck 94 provides both frictional and non-frictional retaining forces or force components to limit rotation of the deformable portion about the neck 94. Additionally, cavities, apertures, or through hole openings of any number, size, or shape may be formed in the neck 94 to receive a portion of the deformable portion 26 to increase the surface area available for contact with the deformable portion 26 and to enhance retention of the deformable portion 26 on the head 14. For example, the head 14 of the fastener 12 shown in FIGS. 12 and 13 includes a hole 46 that extends into and through the neck 94.

Figure 10:
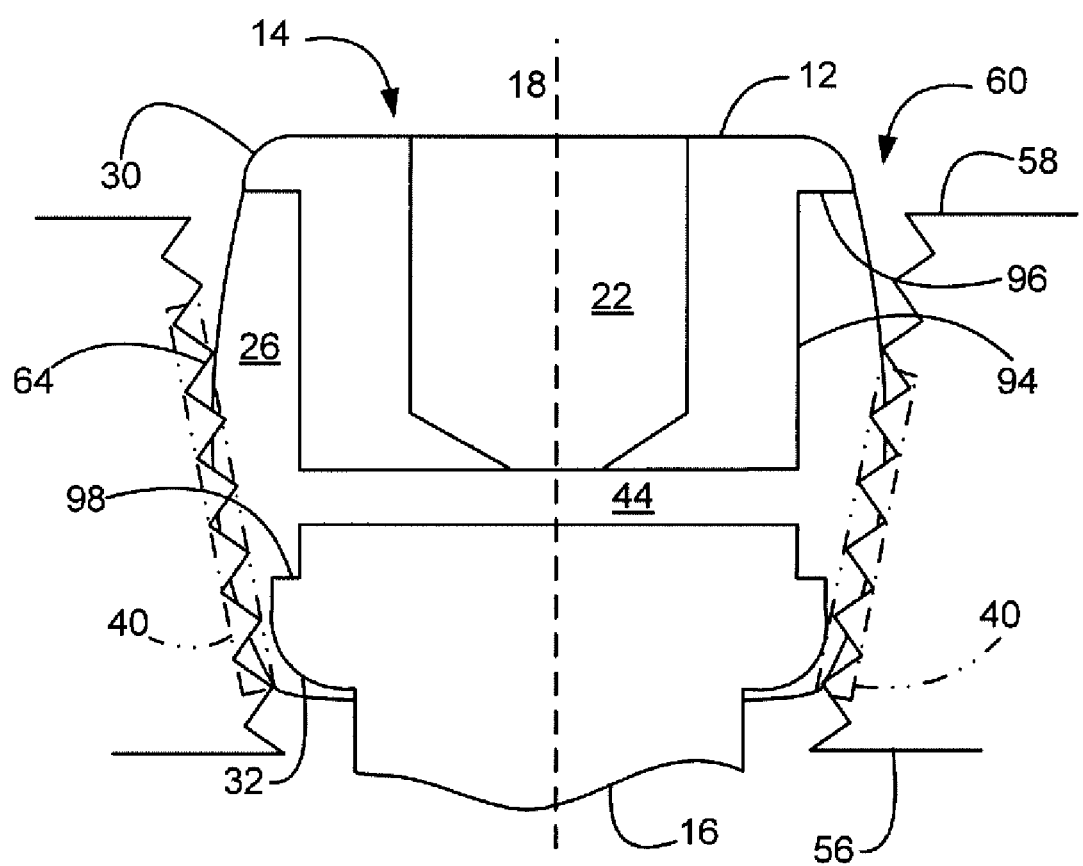
FIG. 10 is a cross-sectional view of a polyaxial fastener inserted in and aligned with the axis of a threaded opening of a bone plate.
Figure 10A:
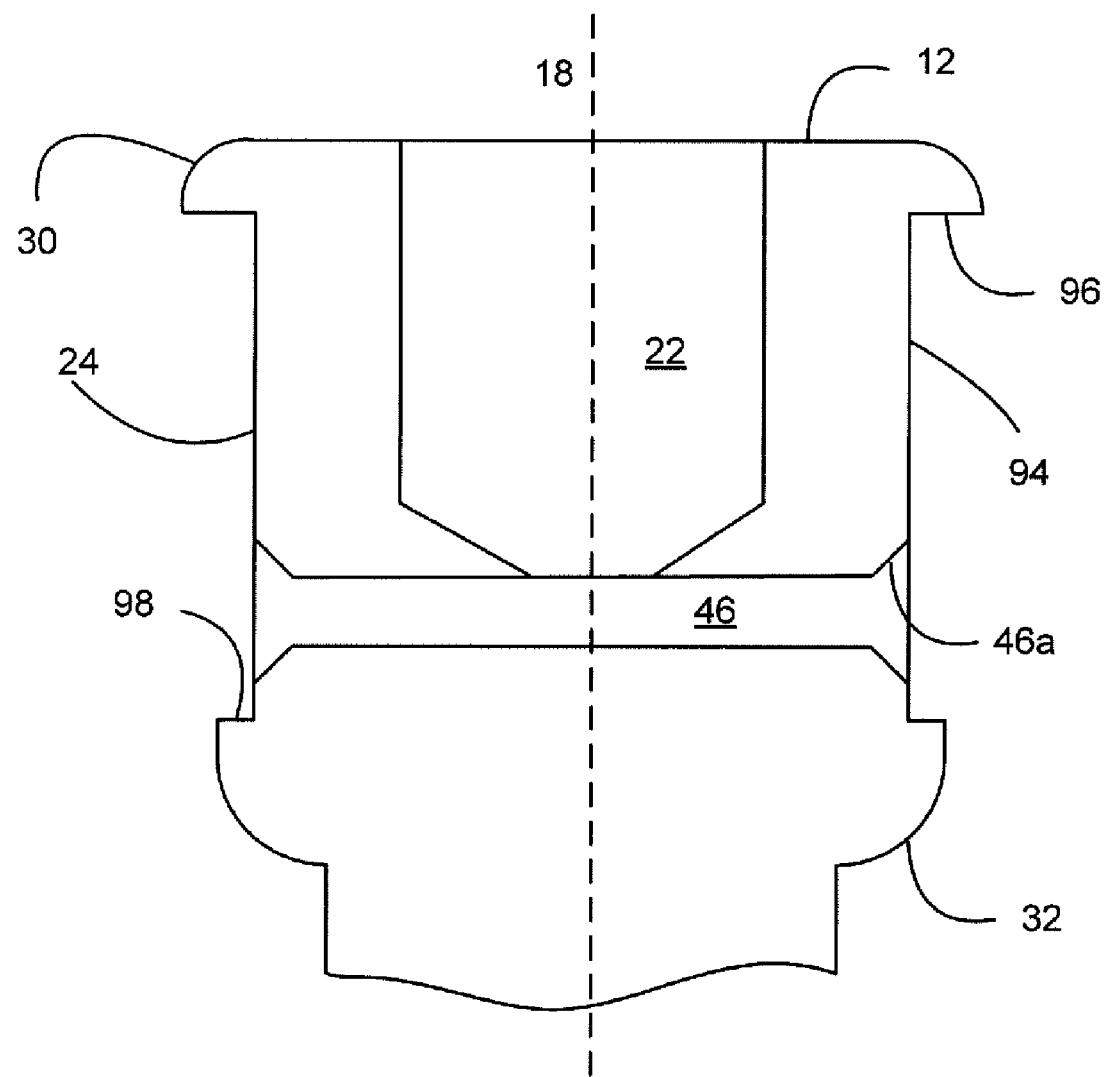
FIG. 10a is a cross-sectional view of a polyaxial fastener.
Figure 11:
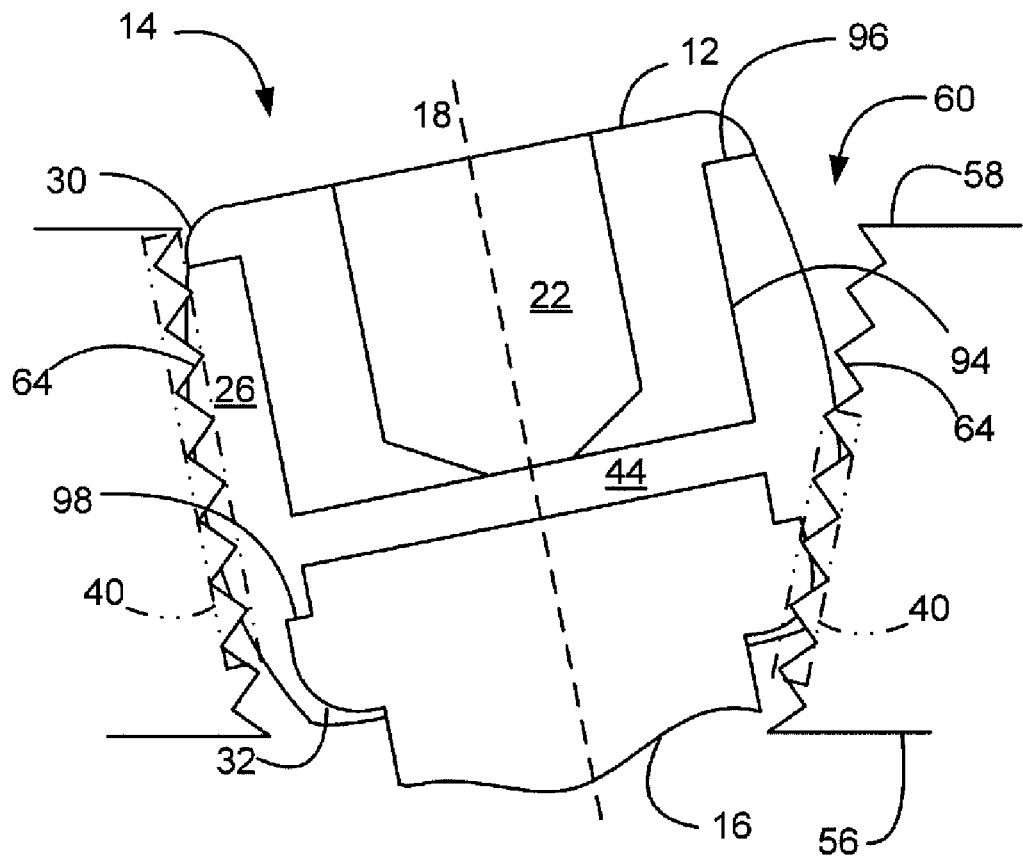
FIG. 11 is a cross-sectional view of the polyaxial fastener of FIG. 10 inserted in and not aligned with the axis of the threaded opening of the bone plate.

As shown in FIG. 12, the hole 46 passes all the way through the neck 94 and intersects the longitudinal axis 18 of the fastener 12. In other examples (not shown), the hole 46 does not pass entirely through the neck 94 but instead only extends partly into the neck 94. Any number of holes 46 may be positioned at any positions on the neck 94 and may extend either entirely through or partially into the neck 94 for receiving a portion of the deformable portion 26 and thereby anchoring it to the head 14. For example, one or more holes 46 may be cross-drilled perpendicular to the longitudinal axis 18 of the fastener 12 before molding the deformable portion 26 onto the head 14. Moreover, the holes 46 may have any cross-sectional shape (e.g., circular, star-shaped, rectilinear, tapered, non-tapered, etc.), and may include a counter-bore 46*a* or tapered or rounded transition from the surface of the neck 94 to the holes 46, as shown in FIG. 10*a*. In some implementations, the neck 94 has a hexagonal cross-sectional shape, and two holes 46 having counter-bore portions are included in the neck 94 such that four faces of the neck include counter-bored openings of the holes 46. If the fastener is molded, the holes 46 are located on faces that do not include parting lines.

When the deformable portion 26 is formed, for example by injection molding the material comprising the deformable portion 26 onto the head 14, the material passes into and fills up the hole 46. When the material solidifies, a rod 44 of material is formed inside the hole 46, as shown in FIG. 13. The rod 44 connects opposite sides of the deformable portion 26 and anchors the deformable portion 26 in position relative to the recess 24 and limits relative rotation between the deformable portion 26 and the head 14 by providing a non-frictional retaining force that opposes a torque force applied to the deformable portion 26.

Figure 14:
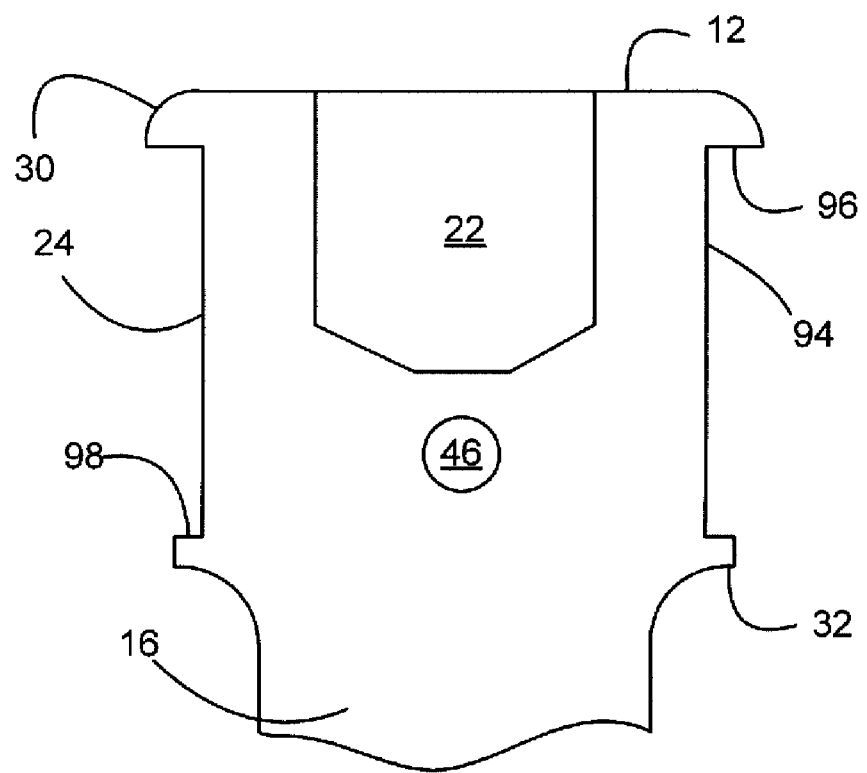
FIG. 14 is a cross-sectional view of the polyaxial fastener shown in FIG. 12.
Figure 15:
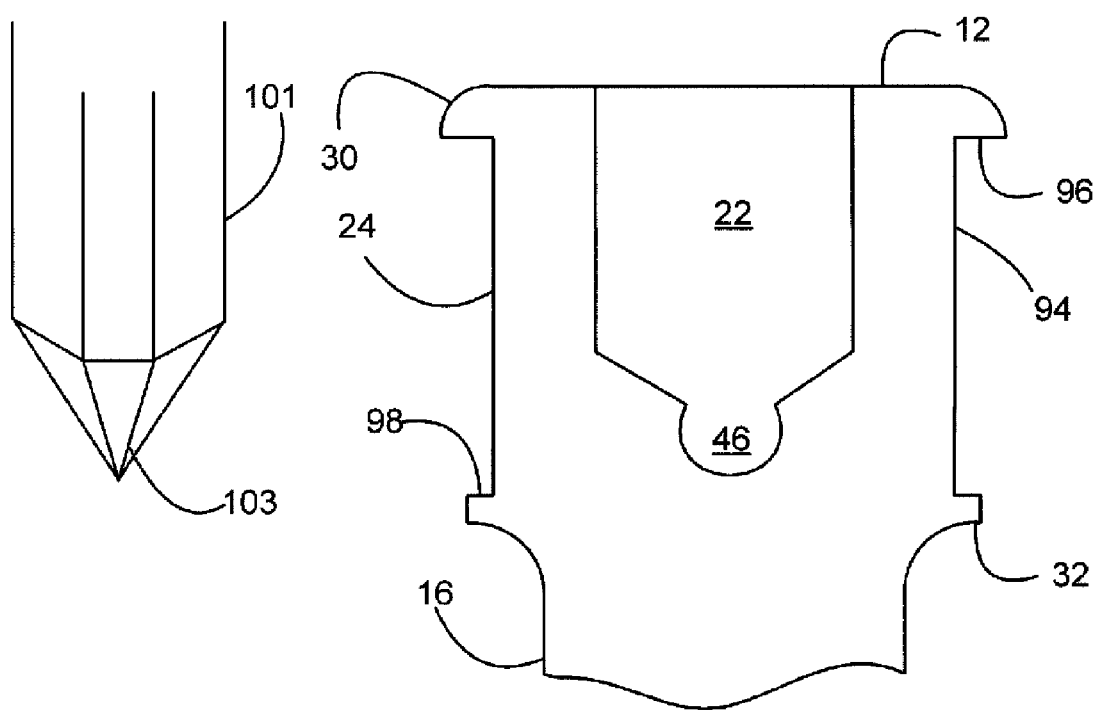
FIG. 15 is a cross-sectional view of a polyaxial fastener head.

In FIGS. 12 and 14, the hole 46 is positioned beneath the bore 22, and the bore 22 does not intersect with the hole 46. Alternatively, as shown in FIG. 15, however, the bore 22 and the hole 46 may intersect, so that an open space is formed between the hole 46 and the bore 22. Thus, when the rod 44 is formed, the rod 44 will be partially exposed and accessible via the bore 22. When exposed to the bore 22, the rod 44 may be useful when a user handles the polyaxial fastener 12 during surgery. For example, a surgeon or other user will typically use a driving tool 101 to insert the polyaxial fastener 12. The surgeon will insert the driving tool 101 within the bore 22, and particularly within the space between the bore 22 and the hole 46. Because the rod 44 is exposed, the surgeon or other user may pierce the rod 44, which is made of the deformable material of the deformable portion 26, with a tooth 103 of the driving tool 101 so that the rod 44 grips the driving tool 101, enabling the surgeon to handle the fastener 12 more easily. Alternatively, the driving tool 101 may include a threaded portion that captures the fastener 12 by engaging a threaded portion of the head 14. After installation, the tooth 103 of the driving tool 101 can be removed from the rod 44 by retracting the driving tool 101 out of the bore 22. Such embodiments may reduce the possibility of the fastener 12 disengaging from the driver 101 during installation.

Figure 16:
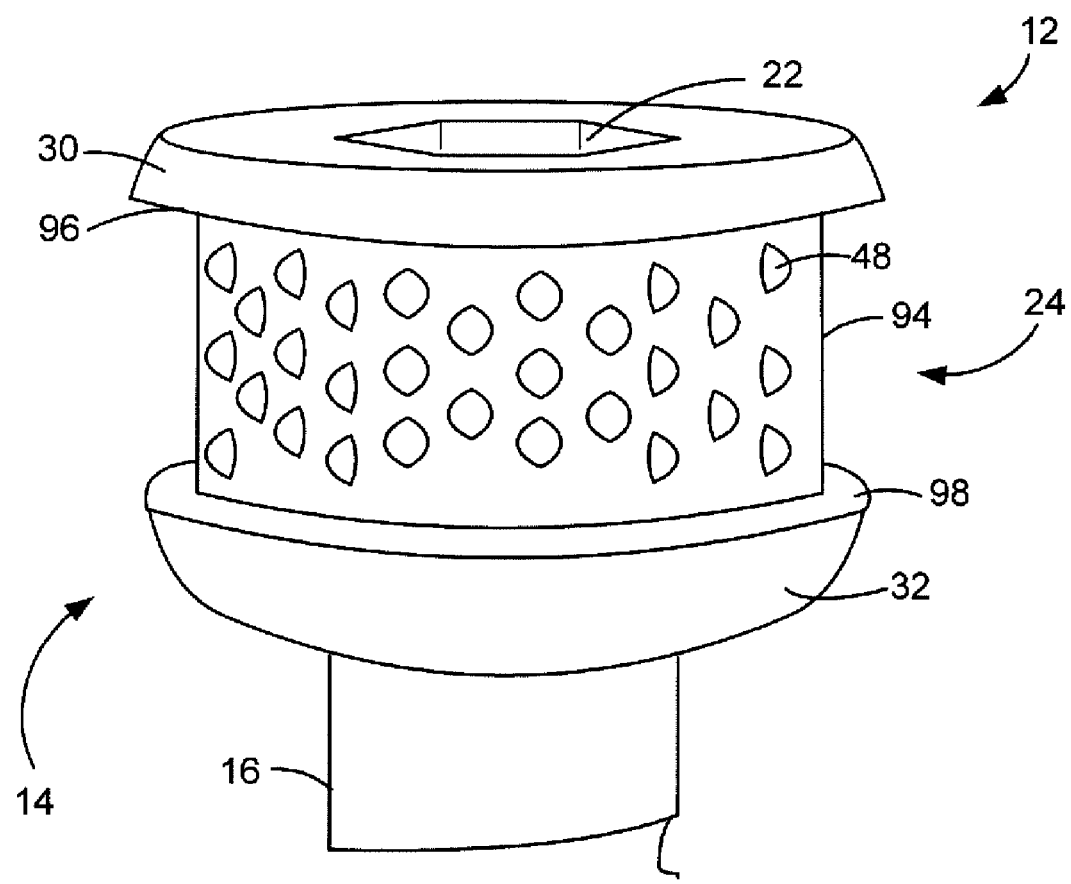
FIGS. 16 and 17 are perspective views of polyaxial fastener heads.
Figure 17:
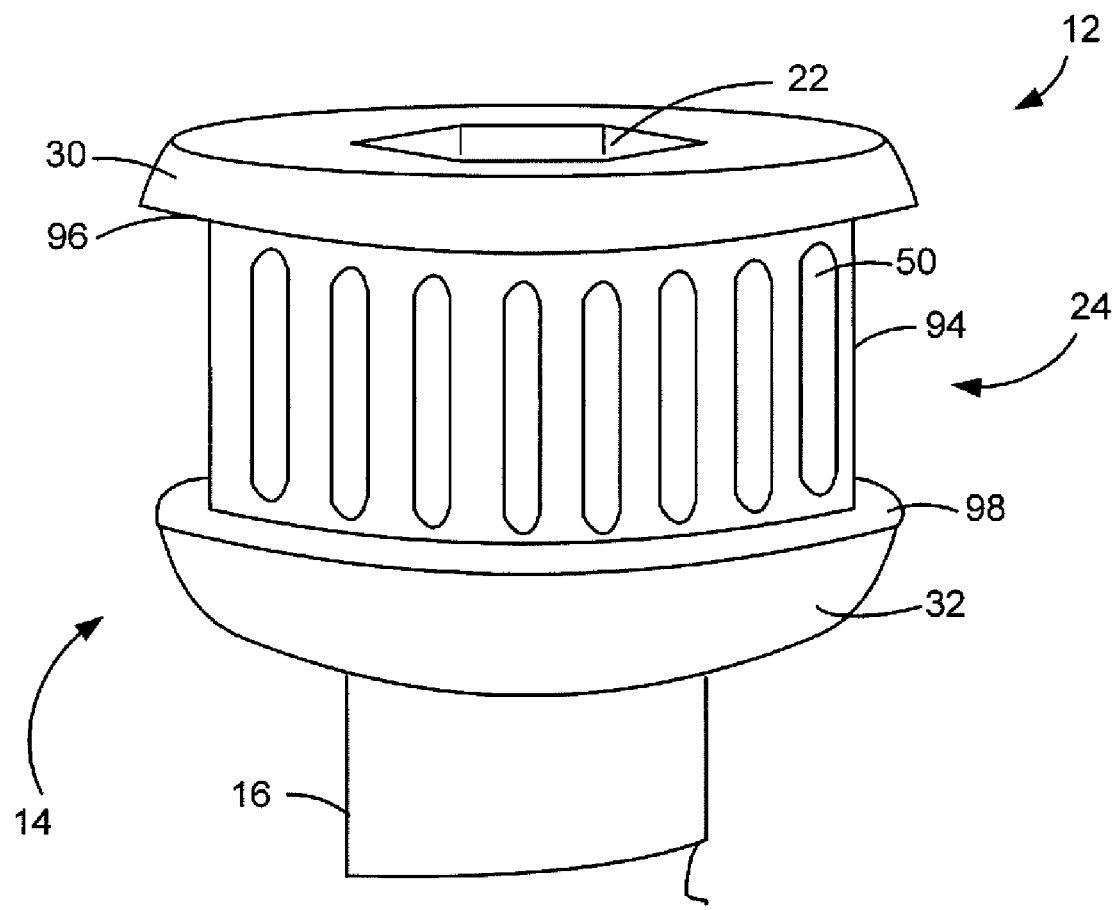

Surface enhancements may also be provided on the surface of the top portion 30, the neck 94, and/or the bottom portion 32 of the head 14 to enhance retention of the deformable portion 26 by providing non-frictional retaining forces in addition to frictional retaining forces. In some embodiments, projections are provided that project from a surface of the top portion 30, the neck 94, and/or the bottom portion 32 and are intended to contact the deformable portion 26. By way only of example, FIG. 16 shows a plurality of bumps 48 on the neck 94. FIG. 17 shows a plurality of raised bars or ribs 50 that are bumps that extend in the longitudinal direction of the polyaxial fastener 12. Again, however, any type of surface enhancements may be provided on the top portion 30, the neck 94, and/or the bottom portion 32. In addition to the apertures and/or projections discussed above, any of the surfaces on head 14 that contact the deformable portion 26 may be embossed, corrugated, knurled, cross-hatched, or roughened to have a texture to enhance adhesion of the deformable portion 26 to the recess 24 and limit slipping and rotation of the deformable portion 26 relative to the neck 94. Although the surface enhancements are described as being on the head 14 of the polyaxial fastener 12, it should be understood that the enhancements may also be included on the inner surface(s) of the deformable portion 26.

Figure 18A:
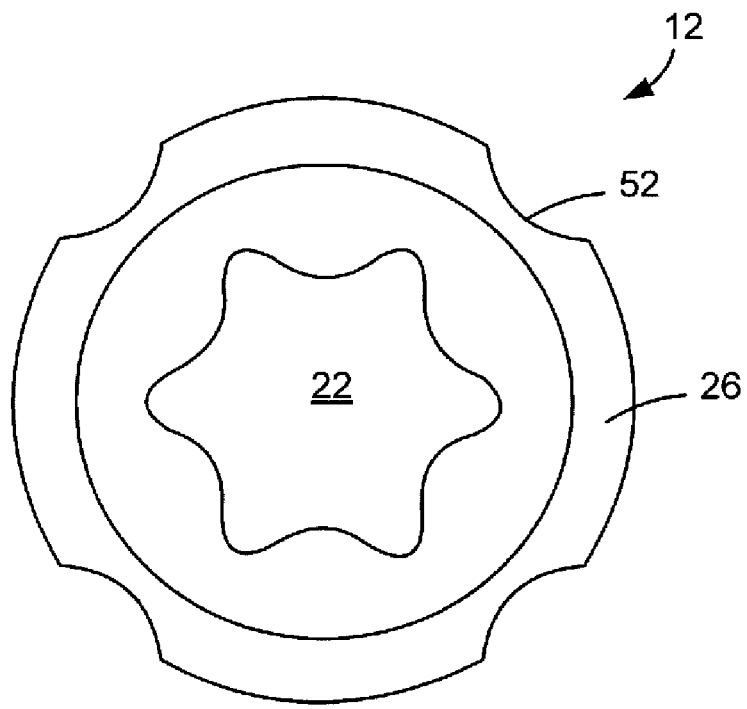
FIG. 18a is a top view of a polyaxial fastener with flutes on the head of the polyaxial fastener.
Figure 18B:
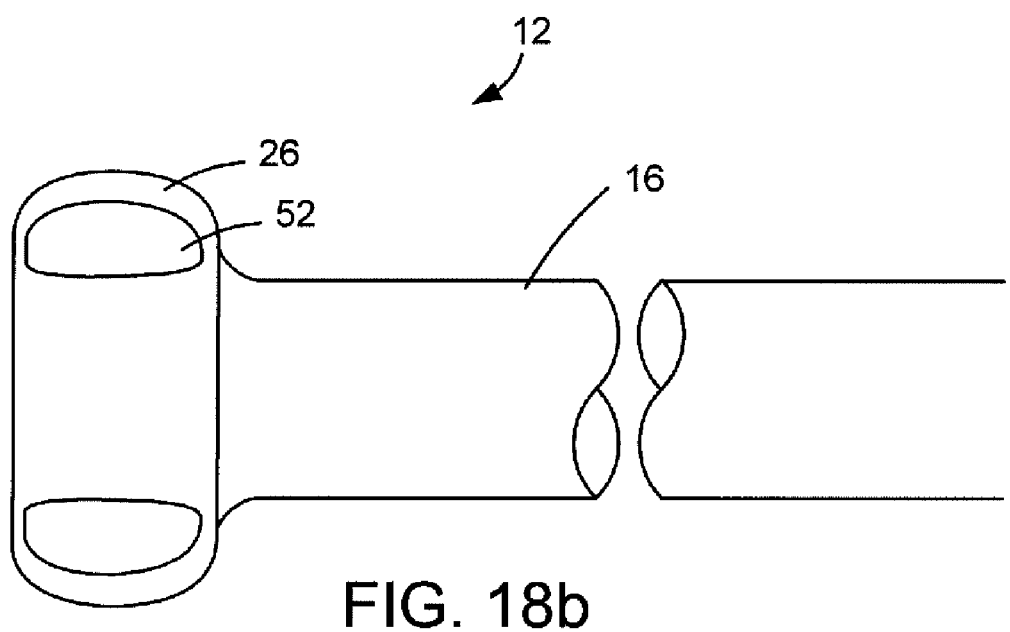

The outer surface of the deformable portion 26 may be shaped or otherwise formed to facilitate insertion of fastener 12. As shown in FIGS. 18*a* and 18*b*, a plurality of flutes 52 are formed around the outer surface of the deformable portion 26. The flutes 52 are shown as four small concave indentions in the deformable portion 26 that are aligned with the longitudinal axis 18 of the polyaxial fastener 12. The flutes 52 provide a lead-in so that the threads 64 of opening 60 can more easily initiate a cut into the deformable portion 26. While four flutes 52 are shown spaced equidistant around the deformable portion 26 of FIGS. 18*a* and 18*b*, flutes 52 may be provided in any number or position to ensure the cutting and securing function desired.

Figure 19:
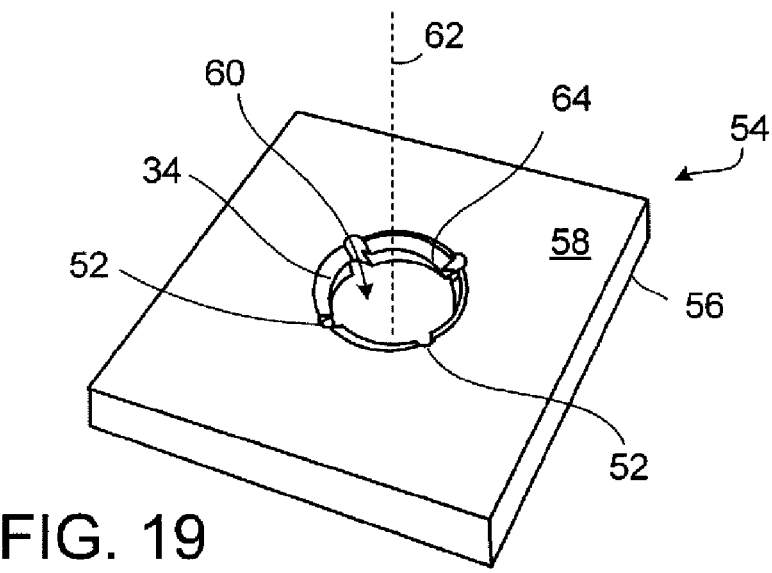
FIG. 19 is a top perspective view of an opening in a bone plate, showing flutes in the opening.

As shown in FIG. 19, the threaded opening 60 has flutes 53. Specifically, the flutes 53 are formed as four small indentions or grooves that interrupt the threads 64. The flutes 53 provide sharp edges of the threads 64 that cut into the deformable portion 26 more easily. The flutes 53 may be smooth and contoured as shown in FIGS. 18 and 19 or they may have any other appropriate shape or size, such as V-shaped, square, or notched. While four flutes 53 are shown spaced equidistant around the threaded opening 60 of FIG. 19, flutes 53 may be provided in any number or position to ensure the cutting and securing function desired.

The fastener 12 can be made by forming a bone engaging portion, forming a head portion that includes a neck portion and a shoulder proximate the neck portion, contacting a deformable portion to the neck portion and/or the shoulder, and providing a retaining structure that retains the deformable portion in contact with the neck portion and/or the shoulder by a force that includes a non-frictional component. For example, forming the bone engaging portion and forming the head portion includes forming the head 14 and the shaft 16 from a monolithic body of stainless steel, such as by molding, machining, casting, and/or other manufacturing techniques. As described above, the head 14 includes the top portion 30 with the top wall 96 and the neck portion 94. Forming the bone engaging portion can include forming a smooth shaft, a threaded shaft, a helical blade, a tack, a deployable talon, and/or an expanding element.

Contacting the deformable portion with the neck portion and/or the shoulder includes, for example, applying a deformable material onto the head 14 in a molding process. The deformable material can include one or more materials such as polyetheretherketone, polyether ketone ketone, self-reinforced polyphenylene, polyphenylsulfone, polysulfone, polyethylene, ultra high molecular weight polyethylene, a carbon composite, resorbable polylactic acid, and polyglycolic acid. In other examples, the deformable material can be applied to the head 14 through an assembly process. A spherical external surface portion, such as the bottom portion 32, can also be formed between the deformable portion and the bone engaging portion. For example, the bottom portion 32 can be formed at the time of forming the head portion, and the deformable material can be molded around the neck 94 between the top portion 30 and the bottom portion 32.

Providing the retaining structure can include forming at least part of the head portion to include a non-circular cross section. For example, the neck 94 can be formed to include a rounded-square cross sectional shape, as illustrated in FIG. 12, and the deformable portion can be formed to include a corresponding shape, as illustrated in FIG. 13. Additionally or alternatively, providing the retaining structure can include forming a bore or a through hole in the head portion, such as the hole 46 (FIG. 12), and forming the deformable portion to include a corresponding structure to engage the bore or through hole, such as the rod 44 (FIG. 13). As another additional or alternative option, the retaining structure can be provided by forming the neck 94, the top wall 96, and/or the bottom wall 98 with one or more protrusion, recess, and/or rough surface texture, and forming the deformable portion with one or more corresponding structures. For example, the neck 94 can be formed to include the bumps 48 and/or the ribs 50 (FIGS. 16 and 17), and the deformable portion, when molded onto the head portion, conforms to the bumps and/or ribs. Grooves or other surface depressions, such as knurling, can be provided on the neck 94 prior to molding the deformable portion on the head 14 such that the deformable portion is formed having corresponding projections that engage the grooves or other surface depressions.

Turning now to the methods of implantation, the surgeon accesses the surgical site of interest, which can be an internal site at which a bone fracture is located that requires stabilization to ensure proper healing. The fracture may be reduced with conventional forceps and guides, which are known to those in the art. A bone plate 54 of appropriate size and shape is placed over the fracture site. In some instances, the bone plate 54 may be temporarily secured to the bone using provisional fixation pins. When using one or more of the bone plates 54 shown in FIGS. 33 and 34, provisional fixation pins may be used through either the provisional fixation holes 86 or any other opening in the plates 54. Provisional fixation provides for temporarily securing the bone plate 54 to the bone so that the surgeon can be certain the bone plate 54 is properly positioned on the fracture site. Moreover, with provisional fixation, x-ray images or other images can be taken of the bone plate 54 construct without excess instruments in the field of view.

In one example of use, the surgeon may then insert a non-locking screw 90 into a threaded opening 60, a non-threaded opening 80, or another opening on one or both sides of the bone fracture to compress the plate 54 against the bone. Then the surgeon may use a polyaxial fastener 12 to further secure any bone fragments that are displaced or separated from the main bone fracture, as shown in FIG. 32.

Figure 33:
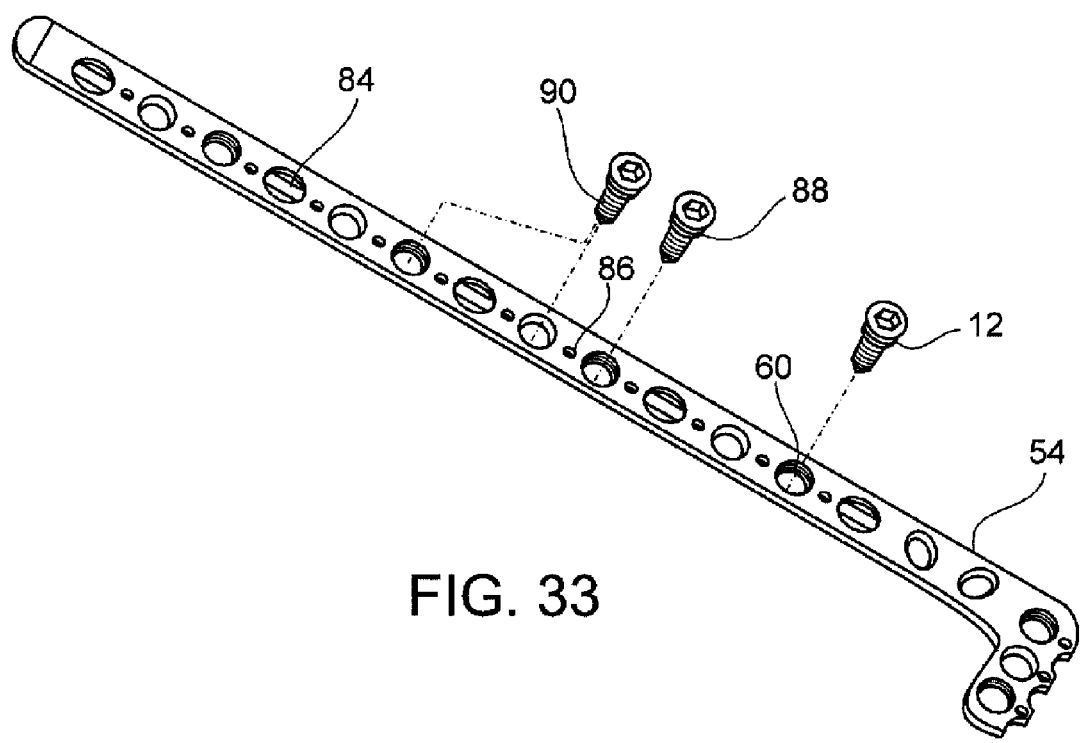
FIG. 33 is a perspective view of a bone plate and fasteners.

When using the polyaxial fastener 12, the surgeon identifies an insertion angle 28 at which to insert the polyaxial fastener 12. If bone plate 54 includes more than one threaded opening 60, as shown in FIGS. 33 and 34, the surgeon also selects the specific threaded opening 60 to be used. After selecting the desired insertion angle 28 and threaded opening 60, the surgeon inserts shaft 16 of polyaxial fastener 12 through threaded opening 60 until the tip 20 contacts bone material. In some cases, a hole may need to be drilled or tapped into the bone along the insertion angle 28 to facilitate the initial tapping and/or insertion of polyaxial fastener 12 into the bone. The surgeon then uses an appropriate driving tool in the bore 22 of the head 14 to manipulate the fastener 12 into place and to apply pressure for insertion.

Figure 32:
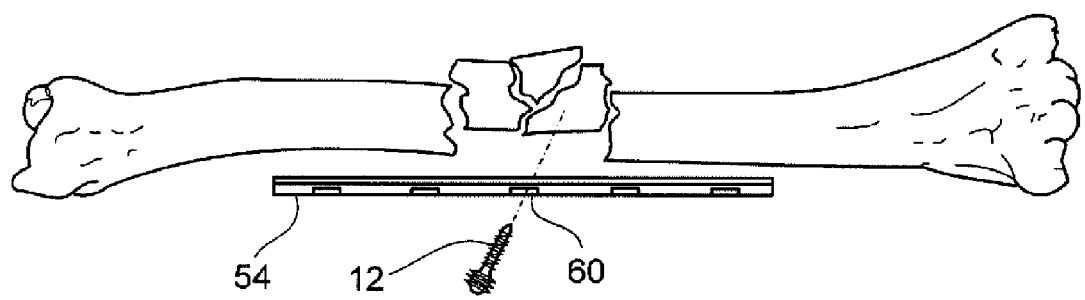
FIG. 32 is a side view of a fracture being treated with a bone plate and polyaxial fastener.

Because polyaxial fastener 12 may be inserted at angles other than in alignment with the central axis 62 of the opening 60, the fastener 12 may be used to grab or secure bone fragments that are out of line with the central axis 62, as shown in FIG. 32. The surgeon may toggle or maneuver the polyaxial fastener 12 in order to secure and draw in displaced bone fragments into desired locations.

Once the bone fragment is moved into the desired location, the polyaxial fastener 12 is ready to be secured to the plate 54. As the fastener 12 is driven further into the bone, the fastener 12 is drawn further into plate 54 and the threads 64 within the threaded opening 60 cut into and deform the deformable portion 26 as described above. If desired, the surgeon may use a torque limiter to ensure that an excessive amount of torque is not applied to the fastener 12 to prevent damage to the deformable portion 26. In some examples, the surgeon may then use additional fasteners 12, traditional locking fasteners 88, and/or non-locking fasteners 90 in other openings of the plate 54. This can help further secure the bone plate 54 to the bone fracture if needed.

It should be understood that the surgeon can insert the polyaxial fastener 12 or screws 88, 90 in any preferred order. For example, the polyaxial fastener 12 may be used for axial compression and/or translation of a bone fragment relative to the bone plate 54. Particularly, a surgeon may insert a non-locking fastener 90 into an opening on a first side of the bone fracture to thereby compress the plate 54 against the bone. Then the surgeon may insert the polyaxial fastener 12 shown in FIGS. 1-7 into a non-threaded 80 or threaded opening 60 having a top portion 72 that includes a compression slope. Movement of the fastener 12 along the compression slope causes relative movement between the bone plate 54 and the underlying bone fragments so that the fragments may be positioned as desired. Finally, the surgeon may then use additional fasteners 12 and/or traditional locking 88 and/or non-locking screws 90 in other openings on the plate 54 to further secure the bone plate 54 to the fracture. A variety of methods, including methods that involve a variety of orders of insertion of various fasteners, are described herein. By no means is the disclosure intended to be limited to methods having only particular steps and/or steps performed in a particular order.

In some instances, once all desired polyaxial fasteners 12 and/or other fasteners are inserted, the surgeon may place covers (not shown) over the unused openings in the plate, particularly if there are any unused openings that span the fracture, in order to strengthen the plate 54. Additionally or alternatively, the surgeon may use bone graft material, bone cement, bone void filler, and/or any other material to help heal the bone.

As explained above, the bone plates 54 for use with the polyaxial fasteners 12 may include any number or variety of holes or openings, including but not limited to all of those disclosed and illustrated herein. Moreover, the plates 54 may also be used with a plurality of different types of fasteners, including polyaxial fasteners 12 and locking and/or non-locking screws. For ease of discussion, the polyaxial fasteners 12 disclosed herein have been described for use with threaded openings 60. However, the fasteners 12 are certainly not limited to use with a threaded opening 60. Instead, the fasteners 12 may be used with any type of opening, including non-threaded openings 80. Different combinations of fasteners 12 and other fasteners may be used in the various openings and inserted in a desired order. Thus the systems 10 described herein give the surgeon options for fracture fixation by providing (1) bone plates 54 that can be used with polyaxial fasteners 12 or other types of fasteners, and (2) polyaxial fasteners 12 that may be used in a variety of different types of openings on a variety of different types of bone plates.

The foregoing description has been presented only for the purposes of illustration and is not intended to be exhaustive or to limit the disclosure to the precise examples disclosed. Many modifications and variations to the structures and methods recited above and shown in the drawings are possible without departing from the scope or spirit of the above disclosure and the following claims. The embodiments were chosen and described to explain principles of the disclosed structures and methods and their practical application so as to enable individuals skilled in the art to make and utilize the structures and methods, including with various modifications that are suited to a particular use. Alternative structures and methods will be apparent to those skilled in the art to which the present disclosure pertains without departing from its spirit and scope.

The invention claimed is:

1. A fastener for engagement with bone, comprising:
   a bone engaging portion;
   a head portion;
   a deformable portion that contacts the head portion, the deformable portion including a material that deforms when the fastener engages one or more fastener-engaging structures of a stabilizing structure; and
   a retaining structure that retains the deformable portion in contact with the head portion by a force that includes a non-frictional component, the retaining structure comprising a through hole defined in the head portion, and further comprising a bore defined in an exterior surface of the fastener such that the bore intersects the through hole, wherein the deformable portion extends into the through hole and is exposed to the bore,
   wherein a portion of the deformable portion that extends into the through hole includes a rod portion that traverses the bore, the rod portion connecting one side of the deformable portion to an opposite side of the deformable portion.

2. A fastener for engagement with bone, comprising:
   a bone engaging portion;
   a head portion;
   a deformable portion that contacts the head portion, the deformable portion including a material that deforms when the fastener engages one or more fastener-engaging structures of a stabilizing structure; and
   a retaining structure that retains the deformable portion in contact with the head portion by a force that includes a non-frictional component, the retaining structure comprising a through hole that is defined in the head portion such that the through hole traverses a width of the head portion, and further comprising a bore defined in an exterior surface of the fastener such that the bore extends along a longitudinal axis of the fastener, wherein the deformable portion extends into the through hole,
   wherein a portion of the deformable portion that extends into the through hole includes a rod portion that traverses the bore, the rod portion connecting one side of the deformable portion to an opposite side of the deformable portion.

3. A fastener for engagement with bone, comprising:
   a bone engaging portion;
   a head portion that includes a top portion, a bottom portion, and a neck between the top and bottom portions, a recess being defined by the top portion, the bottom portion, and the neck; and
   a deformable portion that surrounds the head portion, at least a portion of the deformable portion being retained within the recess of the head portion, the deformable portion including a material that deforms when the fastener engages one or more fastener-engaging structures of a stabilizing structure, the deformable portion being configured to maintain circumferential contact with the head portion during deformation,
   wherein the head portion defines a bore that extends along a longitudinal axis of the fastener, the bore extending into the top portion and the neck of the head portion, and the head portion further defines a through hole that traverses the head portion, and
   wherein the deformable portion includes a rod portion that extends into the through hole to connect one side of the deformable portion to an opposite side of the deformable portion to thereby limit movement of the deformable portion relative to the head portion.

4. The fastener of claim 3, wherein the deformable portion forms a continuous surface around the head portion.

5. A fastener for engagement with bone, comprising:
   a bone engaging portion;
   a head portion that includes a top portion, a bottom portion, and a neck between the top and bottom portions, a recess being defined by the top portion, the bottom portion, and the neck, the head portion defining a bore that extends along a longitudinal axis of the fastener, the bore extending into the top portion and the neck of the head portion, the neck is tapered from the top portion to the bottom portion; and
   a deformable portion that surrounds the head portion, at least a portion of the deformable portion being retained within the recess of the head portion, the deformable portion retained within the recess having a constant thickness throughout its height,
   wherein the head portion further defines a through hole that traverses the head portion, and
   wherein the deformable portion includes a rod portion that extends into the through hole to connect one side of the deformable portion to an opposite side of the deformable portion to thereby limit movement of the deformable portion relative to the head portion.

6. The fastener of claim 5, further comprising a spherical external surface portion disposed between the deformable portion and the bone engaging portion.

7. The fastener of claim 5, wherein at least a portion of the deformable portion comprises a spherical external surface.

8. The fastener of claim 5, wherein the deformable portion forms a continuous surface around the head portion.

9. The fastener of claim 5, wherein the rod portion is exposed to the bore.

10. The fastener of claim 5, wherein the deformable portion includes a material that is cut into and deformed by one or more fastener-engaging structures of a stabilizing structure when the fastener engages the one or more fastener-engaging structures.

11. The fastener of claim 10, wherein the deformable portion has a thickness such that the one or more fastener-engaging structures do not cut entirely through the deformable portion.

12. The fastener of claim 11, wherein a thickness of the deformable portion is between 0.25 mm and 4 mm.

13. The fastener of claim 10, wherein the one or more fastener-engaging structures include internal threads of a threaded opening.

14. The fastener of claim 10, wherein an outer surface of the deformable portion defines a plurality of flutes, the flutes providing a lead-in point for the fastener-engaging structures to cut into.

15. The fastener of claim 14, wherein each of the plurality of flutes are aligned with the longitudinal axis of the fastener.

16. The fastener of claim 15, wherein the plurality of flutes are spaced equidistant from each other around the deformable portion.

17. The fastener of claim 16, wherein the deformable portion defines four or more flutes.

18. The fastener of claim 14, wherein the flutes have a smooth contour.

19. The fastener of claim 14, wherein the flutes are V-shaped, square, or notched.

20. The fastener of claim 5, wherein at least a portion of the bottom portion comprises an external surface that is spherical, conical, or paraboloid.

21. The fastener of claim 5, wherein the bottom portion is sized and shaped such that a tangent line to the bottom portion forms an angle of between 20° and 90° with the longitudinal axis of the fastener.

22. The fastener of claim 5, wherein the deformable portion extends from a top surface of the top portion to a bottom surface of the bottom portion.

23. The fastener of claim 5, wherein the deformable portion extends from a bottom surface of the top portion to a bottom surface of the top portion.

24. The fastener of claim 5, wherein the deformable portion extends from a bottom surface of the top portion to a top surface of the bottom portion.

25. The fastener of claim 5, wherein the neck has a circular cross-section.

26. The fastener of claim 5, wherein the neck has a non-circular cross-section to thereby limit rotation of the deformable portion.

27. The fastener of claim 5, wherein one or more of the top portion, neck, and the bottom portion includes one or more of a protrusion, a recess, and a rough surface texture to thereby limit rotation of the deformable portion.

28. A fastener for engagement with bone, comprising:
a bone engaging portion;
a head portion that includes a top portion, a bottom portion, and a neck between the top and bottom portions, a recess being defined by the top portion, the bottom portion, and the neck, the head portion defining a bore that extends along a longitudinal axis of the fastener, the bore extending into the top portion and the neck of the head portion; and
a deformable portion that surrounds the head portion, at least a portion of the deformable portion being retained within the recess of the head portion, the deformable portion retained within the recess having a constant thickness throughout its height, wherein the thickness is between 0.25 mm and 4 mm, the deformable portion having an outer surface with a plurality of flutes;
wherein head portion further defines a through hole that traverses the head portion, and
wherein the deformable portion includes a rod portion that extends into the through hole to connect one side of the deformable portion to an opposite side of the deformable portion to thereby limit movement of the deformable portion relative to the head portion.

29. The fastener of claim 28, further comprising a spherical external surface portion disposed between the deformable portion and the bone engaging portion.

30. The fastener of claim 28, wherein at least a portion of the deformable portion comprises a spherical external surface.

31. The fastener of claim 28, wherein the deformable portion forms a continuous surface around the head portion.

32. The fastener of claim 28, wherein the rod portion is exposed to the bore.

33. The fastener of claim 28, wherein the deformable portion includes a material that is cut into and deformed by one or more fastener-engaging structures of a stabilizing structure when the fastener engages the one or more fastener-engaging structures.

34. The fastener of claim 33, wherein the deformable is configured to be not cut entirely through by the one or more fastener-engaging structures.

35. The fastener of claim 33, wherein the one or more fastener-engaging structures include internal threads of a threaded opening.

36. The fastener of claim 28, wherein at least a portion of the bottom portion comprises an external surface that is spherical, conical, or paraboloid.

37. The fastener of claim 28, wherein the bottom portion is sized and shaped such that a tangent line to the bottom portion forms an angle of between 20° and 90° with the longitudinal axis of the fastener.

38. The fastener of claim 28, wherein the deformable portion extends from a top surface of the top portion to a bottom surface of the bottom portion.

39. The fastener of claim 28, wherein the deformable portion extends from a bottom surface of the top portion to a bottom surface of the top portion.

40. The fastener of claim 28, wherein the deformable portion extends from a bottom surface of the top portion to a top surface of the bottom portion.

41. The fastener of claim 28, wherein the neck has a circular cross-section.

42. The fastener of claim 28, wherein the neck has a non-circular cross-section to thereby limit rotation of the deformable portion.

43. The fastener of claim 28, wherein one or more of the top portion, neck, and the bottom portion includes one or more of a protrusion, a recess, and a rough surface texture to thereby limit rotation of the deformable portion.

44. The fastener of claim 33, wherein the plurality of flutes are configured to provide a lead-in point for the fastener-engaging structures to cut into.

45. The fastener of claim 44, wherein each of the plurality of flutes are aligned with the longitudinal axis of the fastener.

46. The fastener of claim 45, wherein the plurality of flutes are spaced equidistant from each other around the deformable portion.

47. The fastener of claim 46, wherein the deformable portion defines four or more flutes.

48. The fastener of claim 44, wherein the flutes have a smooth contour.

49. The fastener of claim 44, wherein the flutes are V-shaped, square, or notched.

* * * * *